(12) United States Patent
Chuntharapai et al.

(10) Patent No.: US 7,252,994 B2
(45) Date of Patent: Aug. 7, 2007

(54) HUMAN DR4 ANTIBODIES AND USES THEREOF

(75) Inventors: Anan Chuntharapai, Colma, CA (US); Kyung Jin Kim, Cupertino, CA (US)

(73) Assignee: Genentech, Inc., South San Francisco, CA (US)

( * ) Notice: Subject to any disclaimer, the term of this patent is extended or adjusted under 35 U.S.C. 154(b) by 323 days.

(21) Appl. No.: 10/480,730

(22) PCT Filed: Jun. 29, 2002

(86) PCT No.: PCT/US02/20712

§ 371 (c)(1),
(2), (4) Date: Dec. 12, 2003

(87) PCT Pub. No.: WO03/066661

PCT Pub. Date: Aug. 14, 2003

(65) Prior Publication Data

US 2004/0147725 A1 Jul. 29, 2004

Related U.S. Application Data

(60) Provisional application No. 60/303,220, filed on Jul. 3, 2001.

(51) Int. Cl.
*A61K 39/395* (2006.01)
*C12N 5/18* (2006.01)

(52) U.S. Cl. .................. 435/334; 435/344; 424/142.1; 424/143.1; 424/155.1; 530/388.15; 530/388.22; 530/388.8; 530/391.3; 530/391.7; 530/350

(58) Field of Classification Search ..................... None
See application file for complete search history.

(56) References Cited

U.S. PATENT DOCUMENTS

| | | | |
|---|---|---|---|
| 5,677,165 | A | 10/1997 | de Boer et al. |
| 6,342,383 | B1 | 1/2002 | Perron et al. |
| 6,433,147 | B1 | 8/2002 | Ni et al. |
| 6,461,823 | B1 | 10/2002 | Ni et al. |
| 6,943,020 | B2 | 9/2005 | Ni et al. |
| 6,989,144 | B1 * | 1/2006 | Busfield et al. |
| 7,060,272 | B2 | 6/2006 | Ni et al. |
| 2003/0036168 | A1 | 2/2003 | Ni et al. |
| 2003/0073187 | A1 | 4/2003 | Ni et al. |
| 2003/0108516 | A1 | 6/2003 | Ni et al. |
| 2003/0133932 | A1 | 7/2003 | Zhou et al. |
| 2004/0120947 | A1 * | 6/2004 | Ashkenazi et al. |
| 2004/0180049 | A1 * | 9/2004 | Ashkenazi et al. |

FOREIGN PATENT DOCUMENTS

| | | |
|---|---|---|
| EP | 0388151 A1 * | 3/1990 |
| EP | 417563 | 3/1991 |
| EP | 870827 | 10/1998 |
| WO | WO 92/15698 | 9/1992 |
| WO | WO 97/01633 | 1/1997 |
| WO | WO 97/25428 | 7/1997 |
| WO | WO 98/18921 | 5/1998 |
| WO | WO 98/28426 | 7/1998 |
| WO | WO 98/32856 | 7/1998 |
| WO | WO 98/35986 | 8/1998 |
| WO | WO 98/39361 | 9/1998 |
| WO | WO 98/41629 | 9/1998 |
| WO | WO 98/46643 | 10/1998 |
| WO | WO 98/46751 | 10/1998 |
| WO | WO 98/51793 | 11/1998 |
| WO | WO 99/02653 | 1/1999 |
| WO | WO 99/04001 | 1/1999 |
| WO | WO 99/07738 | 2/1999 |
| WO | WO 99/09165 | 2/1999 |
| WO | WO 99/11791 | 3/1999 |
| WO | WO 99/33980 | 7/1999 |
| WO | WO 99/37684 | 7/1999 |
| WO | WO 99/64461 | 12/1999 |
| WO | WO 00/73349 A1 | 12/2000 |
| WO | WO 02/097033 | 12/2002 |
| WO | WO 03/037913 | 5/2003 |
| WO | WO 03/038043 | 5/2003 |
| WO | WO 03/042367 | 5/2003 |

OTHER PUBLICATIONS

Bodmer et al., TRAIL receptor-2 signals apoptosis through FADD and caspase-8, Nat. Cell Biol., 2:241-243, Apr. 2000.*
Srivastava, R.K., TRAIL/Apo-2L: Mechanisms and Clinical Applications in Cancer, Neoplasia, vol. 3, No. 6, 2001, pp. 535-546.
Chuntharapai, et al., Isotype-Dependent Inhibition of Tumor Growth In Vivo by Monoclonal Antibodies to Death Receptor 4, Journal of Immunology, vol. 166, No. 8, Apr. 15, 2001, pp. 4891-4898.
Amakawa et al., "The Hodgkin Disease Antigen CD30 is Crucial for Antigen-Induced Death of Developing T Cells" *Symposium on Programmed Cell Death* (Abstract No. 10), Cold Spring Harbor Laboratory (1995).
Anderson et al., "A Homologue of the TNF Receptor and Its Ligand Enhance T-Cell Growth and Dendritic-Cell Function." *Nature*. 390(6656):175-179 (Nov. 13, 1997).
Armitage et al., "Molecular and Biological Characterization of a Murine Ligand for CD40." *Nature*. 357(6373):80-82 (1992).
Ashkenazi and Dixit, "Apoptosis control by death and decoy receptors" *Current Opinion in Cell Biology* 11(2):255-269 (1999).
Ashkenazi and Dixit, "Death Receptors: Signaling and Modulation." *Science*. 281(5381):1305-1308 (1998).
Ashkenazi et al., "Apoptosis regulation by death and decoy receptors" *FASEB journal* 13:A1336 (Apr. 23, 1999).
Ashkenazi et al., "Safety and antitumor activity of recombinant soluble Apo2 ligand" *Journal of Clinical Investigation* 104(2):155-162 (1999).

(Continued)

*Primary Examiner*—Lorraine Spector
*Assistant Examiner*—Claire M. Kaufman
(74) *Attorney, Agent, or Firm*—Diane L. Marschang; Sidley Austin LLP

(57) ABSTRACT

Human Death Receptor 4 (DR4) antibodies are provided. The human DR4 antibodies may be included in pharmaceutical compositions, articles of manufacture, or kits. Methods of treatment and diagnosis using the DR4 antibodies are also provided.

27 Claims, 25 Drawing Sheets

OTHER PUBLICATIONS

Bachmann et al., "TRANCE, A Tumor Necrosis Factor Family Member Critical for CD40 Ligand-Independent T Helper Cell Activation." *J. Experimental Medicine*. 189:1025-1031 (1999).
Baldwin, A., "The NF-κB and YκB Proteins: New Discoveries and Insights" *Ann. Rev. Immunol.* 14:649-683 (1996).
Banner et al., "Crystal Structure of the Soluble Human 55 kd TNF Receptor-Human TNFβ Complex: Implications for TNF Receptor Activation" *Cell* 73:431-445 (1993).
Bodmer et al., "Cysteine 230 Is Essential for the Structure and Activity of the Cytotoxic Ligand TRAIL" *Journal of Biological Chemistry* 275:20632-20637 (2000).
Bodmer et al., "TRAMP, A Novel Apoptosis-Mediating Receptor with Sequence Homology to Tumor Necrosis Factor Receptor 1 and Fas(Apo-1/CD95)." *Immunity*. 6:79-88 (1997).
Brockhaus et al., "Identification of Two Types of Tumor Necrosis Factor Receptors on Human Cell Lines by Monoclonal Antibodies." *Proc. Natl. Acad. Sci. USA* 87:3127-3131 (1990).
Brojatsch et al., "CAR1, A TNFR-Related Protein, Is a Cellular Receptor for Cytopathic Avian Leukosis-Sarcoma Viruses and Mediates Apoptosis." *Cell*. 87:845-855 (1996).
Browning et al., "Lymphotoxin β, a Novel Member of the TNF Family That Forms a Heteromeric Complex with Lymphotoxin on the Cell Surface" *Cell* 72:847-856 (1993).
Chicheportiche et al., "TWEAK, A New Secreted Ligand in the Tumor Necrosis Factor Family that Weakly Induces Apoptosis." *Journal of Biological Chemistry* 272(51):32401-32410 (1997).
Chinnaiyan et al., "Combined effect of tumor necrosis factor-related apoptosis-inducing ligand and ionizing radiation in breast cancer therapy" *Proc. Natl. Acad. Sci.* 97:1754-1759 (2000).
Chinnaiyan et al., "Signal Transduction by DR3, A Death Domain-Containing Receptor Related to TNFR-1 and CD95." *Science*. 274:990-992 (1996).
Chuntharapai et al., "The induction and blocking of apoptosis by anti Apo2 monoclonal antibodies" *FASEB Journal* (Annual Meeting of the Professional Research Scientists for Experimental Biology) 13(4):A518 (1999).
Dealtry et al., "DNA Fragmentation and Cytotoxicity Caused by Tumor Necrosis Factor is Enhanced by Interferon-γ" *European Journal of Immunology* 17:689-693 (1987).
Degli-Esposti et al., "Cloning and Characterization of TRAIL-R3, a Novel Member of the Emerging TRAIL Receptor Family" *Journal of Experimental Medicine* 186(7):1165-1170 (1997).
Degil-Esposti et al., "The Novel Receptor TRAIL-R4 Induces NF-κB and Protects against TRAIL-Mediated Apoptosis, yet Retains an Incomplete Death Domain" *Immunity* 7:813-820 (1997).
Emery et al., "Osteoprotegerin is a Receptor for the Cytotoxic Ligand Trail." *J. Bio. Chem.* 273(23):14363-14367 (1998).
Gazitt, Y., "TRAIL is a potent inducer of apoptosis in myeloma cells derived from multiple myeloma patients and its not cytotoxic to hematopoietic stem cells" *Leukemia* 13:1817-1824 (1999).
Gliniak and Le, "Tumor Necrosis Factor-related Apoptosis-inducing Ligand's Antitumor Activity in Vivo Is Enhanced by the Chemoptherapeutic Agent CPT-11" *Cancer Research* 59:6153-6158 (1999).
Golstein, P., "Cell Death: TRAIL and its Receptors" *Curr. Biol* 7:R750-R753 (1997).
Goodwin et al., "Molecular Cloning and Expression of the Type 1 and Type 2 Murine Receptors for Tumor Necrosis Factor." *Mol. Cell. Bio.* 11:3020-3026 (1991).
Gras et al., "BCMAp: An Integral Membrane Protein in the Golgi Apparatus of Human Mature B Lymphocytes." *Int. Immunology.* 7:1093-1106 (1995).
Green and Flavell., "TRANCE-RANK, A New Signal Pathway Involved in Lymphocyte Development and T Cell Activation." *J. Experimental Medicine*. 189:1017-1020 (Apr. 1999).
Griffith et al., "Monocyte-mediated Tumoricidial Activity via the Tumor Necrosis Factor-related Cytokine, TRAIL" *Journal of Experimental Medicine* 189:1343-1353 (1999).
Gruss and Dower, "Tumor Necrosis Factor Ligand Superfamily: Involvement in the Pathology of Malignant Lymphomas" *Blood* 85:3378-3404 (1995).

Hahne et al., "Apr. A New Ligand of the Tumor Necrosis Factor Family, Stimulates Tumor Cell Growth." *Journal of Experimental Medicine* 188(6):1185-1190 (1998).
Hale et al., "Demonstration of In Vitro and In Vivo Efficacy of Two Biologically Active Human Soluble TNF Receptors Expressed in *E. coli*." *J. Cell. Biochem*. (abstract only, suppl. 15F; P 424) pp. 113 (1991).
Hillier et al., "Generation and Analysis of 280,000 Human Expressed Sequence Tags" *Genome Research* 6(9):807-828 (1996).
Hohman et al., "Two Different Cell Types Have Different Major Receptors for Human Tumor Necrosis Facotr (TNFα)" *Journal of Biological Chemistry* 264:14927-14934 (1989).
Hymowitz et al., "A unique zinc-binding site revealed by the high-resolution X-ray structure of homotrimeric Apo2L/TRAIL" *Biochemistry* 39(4):633-640 (2000).
Hymowitz et al., "Triggering Cell Death: The Crystal Structure of Apo2L/TRAIL in a Complex with Death Receptor 5." *Molecular Cell*. 4(4):563-571 (1999).
Itoh et al., "The Polypeptide Encoded by the cDNA for Human Cell Surface Antigen Fas Can Mediate Apoptosis." *Cell*. 66:233-243 (1991).
Jo et al., "Apoptosis induced in normal human hepatocytes by tumor necrosis factor-related apoptosis-inducing ligand" *Nature Medicine* 6(5):564-567 (2000).
Johnsen et al., "Regulation of Apo-2 Ligand/TRAIL Expression in NK cells-Involvement in NK Cell-Mediated Cytotoxicity" *Cytokine* 11:664-672 (1999).
Johnson et al., "Expression and Structure of the Human NGF Receptor" *Cell* 47:545-554 (1986).
Josien et al., "TRANCE, A TNF Family Member, Is Differentially Expressed on T Cell Subsets and Induces Cytokine Production in Dendritic Cells." *J. Immunol.* 162:2562-2568 (1999).
Josien et al., "TRANCE, A Tumor Necrosis Factor Family Member, Enhances the Longevity and Adjuvant Properties of Dendritic Cells In Vivo." *Journal of Experimental Medicine* 191:495-501 (Feb 2000).
Keane, et al., "Chemotherapy Augments TRAIL-induced Apoptosis in Breast Cell Lines" *Cancer Research* 59:734-741 (Feb. 1, 1999).
Kitson et al., "A Death-Domain-Containing Receptor that Mediate Apoptosis" *Nature* 384:372-375 (1996).
Kohno et al., "A Second Tumor Necrosis Factor Receptor Gene Product Can Shed a Naturally Occuring Tumor Necrosis Factor Inhibitor." *Proc. Natl. Acad. Sci. USA* 87:8331-8335 (1990).
Kong et al., "Activated T Cells Regulate Bone Loss and Joint Destruction in Adjuvant Arthritis through Osteoprotegerin Ligand" *Nature* 402(6759):304-309 (1999).
Kong et al., "OPGL is a Key Regulator of Osteoclastogenesis, Lymphocyte Development and Lymph-Node Organogenesis." *Nature*. 397:315-323 (Jan. 1999).
Krammer et al., "Regulation of Apoptosis in the Immune System" *Curr. Op. Immunol*. 6:279-289 (1994).
Laabi et al., "A New Gene, BCM, on Chromosome 16 is Fused to the Interleukin 2 Gene by a t(4;16) (q26;p13) Translocation in a Malignant T Cell Lymphoma." *EMBO Journal*. 11:3897-3904 (1992).
Laabi et al., "The BCMA Gene, Preferentially Expressed During B Lymphoid Maturation, is Bidirectionally Transcribed." *Nucleic Acids Research.* 22:1147-1154 (1994).
Lacey et al., "Osteoprotegerin Ligand is a Cytokine That Regulates Osteoclast Differentiation and Activation." *Cell* 93(2):165-176 (Apr. 17, 1998).
Lawrence et al., "Differential hepatocyte toxicity of recombinant Apo2L/TRAIL versions" *Nature Medicine* 7(4):383-385 (Apr. 2001).
Lewis et al., "Cloning and Expression of cDNAs for Two Distinct Murine Tumor Necrosis Factor Receptors Demonstrate One Receptor is Species Specific." *PNAS USA.* 88:2830-2834 (1991).
Locksley et al., "The TNF and TNF Receptor Superfamilies: Integrating Mammalian Biology" *Cell* 104:487-501 (Feb. 23, 2001).
Loetscher et al., "Molecular Cloning and Expression of the Human 55 kd Tumor Necrosis Factor Receptor" *Cell* 61:351-359 (1990).
Lotz et al., "The Nerve Growth Factor/Tumor Necrosis Factor Receptor Family." *J. Leukocyte Biol.* 60:1-7 (1996).

MacFarlane et al., "Identification and Molecular Cloning of Two Novel Receptors for the Cytotoxic Ligand TRAIL" *Journal of Biological Chemistry* 272(41)):25417-25420 (1997).

Mackay et al., "Mice Transgenic for BAFF Develop Lymphocytic Disorders Along with Autoimmune Manifestations" *Journal of Experimental Medicine* 190:1697-1710 (1999).

Madry et al., "The Characterization of Murine BCMA Gene Defines it as a New Member of the Tumor Necrosis Factor Receptor Superfamily." *Int. Immunology*. 10:1693-1702 (1998).

Mallet et al., "Characterization of the MRC OX40 Antigen of Activated CD4 Positive T Lymphocytes—A Molecule Related to Nerve Growth Factor Receptor." *EMBO Journal* 9(4):1063-1068 (1990).

Mariani et al., "Interleukin 1β-converting Enzyme Related Protease/Caspases Are Involved in TRAIL-induced Apoptosis of Myeloma and Leukemia Cells" *Journal of Cell Biology* 137:221-229 (1997).

Marsters et al., "A Novel Receptor for Apo2L/TRAIL Contains a Truncated Death Domain" *Current Biology* 7:1003-1006 (1997).

Marsters et al., "Activation of Apoptosis by Apo-2 Ligand is Independent of FADD but Blocked by CrmA." *Current Biology*. 6(6):750-752 (1996).

Marsters et al., "Apo-3, A New Member of the Tumor Necrosis Factor Receptor Family, Contains a Death Domain and Activates Apoptosis and NF-κB." *Curr. Biol*. 6(12):1669-1676 (1996).

Marsters et al., "Herpesvirus Entry Mediator, A Member of the Tumor Necrosis Factor Receptor (TNFR) Family, Interacts with Members of the TNFR-Associated Factor Family and Activates the Transcription Factors NF-κB and AP-1." *J. Bio. Chem*. 272(22):14029-14032 (1997).

Marsters et al., "Identification of a Ligand for the Death-Domain-Containing Receptor Apo3." *Current Biology*. 8(9):525-528 (1998).

Mizutani et al., "Synergistic Cytotoxicity and Apoptosis by Apo-2 Ligand and Adriamycin against Bladder Cancer Cells" *Clin. Cancer Res*. 5:2605-2612 (1999).

Mongkolsapaya et al., "Cutting Edge: Lymphocyte Inhibitor of TRAIL (TNF-Related Apoptosis-Inducing Ligand) : A New Receptor Protecting Lymphocytes From the Death Ligand TRAIL." *J. Immunol*. 160(1):3-6 (1998).

Montgomery et al., "Herpes Simplex Virus-1 Entry into Cells Mediated by a Novel Member of the TNF/NGF Receptor Family" *Cell* 87(3):427-436 (1996).

Moore et al., "BLyS: Member of the Tumor Necrosis Factor Family and B Lymphocyte Stimulator." *Science*. 285(5425):260-263 (1999).

Mukhopadhyay et al., "Identification and Characterization of a Novel Cytokine, THANK, a TNF Homologue That Activates Apoptosis, Nuclear Factor-κB, and c-Jun NH$_2$-Terminal Kinase" *J. Bio. Chem*. 274:15978-15981 (1999).

Nagata and Golstein, "The Fas Death Factor" *Science* 267:1449-1456 (1995).

Nagata, S., "Apoptosis by Death Factor." *Cell*. 88:355-365 (Feb. 1997).

Nagata, S., "Steering anti-cancer drugs away from the TRAIL" *Nature Medicine* 6(5):502-503 (May 2000).

Nocentini et al., "A New Member of the Tumor Necrosis Factor/Nerve Growth Factor Receptor Family Inhibits T Cell Receptor-Induced Apoptosis." *Proc. Natl. Acad. Sci*. 94(12):6216-6221 (1997).

Nophar et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and a Soluble Form of the Receptor." *EMBO Journal*. 9:3269-3278 (1990).

Pan et al., "An Antagonist Decoy Receptor and a Death-Domain Containing Receptor for TRAIL." *Science*. 277:815-818 (Aug. 1997).

Pan et al., "Identification and Functional Characterization of DR6, A Novel Death Domain-Containing TNF Receptor." *FEBS Letters*. 431(3):351-356 (1998).

Pan et al., "The Receptor for the Cytotoxic Ligand TRAIL." *Science*. 276:111-113 (Apr. 4, 1997).

Pan et al., "TRUNDD, A New Member of the TRAIL Receptor Family That Antagonize TRAIL Signalling." *FEBS Letters*. 424(1-2):41-45 (1998).

Pitti et al., "Genomic Amplification of a Decoy Receptor for Fas Ligand in Lung and Colon Cancer." *Nature*. 396(6712):699-703 (1998).

Pitti et al., "Induction of Apoptosis by Apo-2 Ligand, a New Member of the Tumor Necrosis Factor Cytokine Family" *Journal of Biological Chemistry* 271:12687-12690 (1996).

Qin et al., "Avoiding premature apoptosis of normal epidermal cells" *Nature Medicine* 7(4):385-386 (Apr. 2001).

Radeke et al., "Gene Transfer and Molecular Cloning of the Rat Nerve Growth Factor Receptor." *Nature*. 325:593-597 (1987).

Renshaw et al., "Humoral Immune Responses in CD40 Ligand-deficient Mice" *Journal of Experimental Medicine* 180:1889-1900 (1994).

Rieger et al, "APO2 ligand: a novel lethal weapon against malignant glioma?" *FEBS Letters* 427:124-128 (1998).

Roth et al., "Locoregional Apo2L/TRAIL Eradicates Intracranial Human Malignant Giloma Xenografts in Athymic Mice in the Absence of Neurotoxicity" *Biochem. Biophys. Res. Comm* 265:479-483 (1999).

Schall et al., "Molecular Cloning and Expression of a Receptor for Human Tumor Necrosis Factor" *Cell* 61:361-370 (1990).

Schmid et al., "DNA Fragmentation: Manifestation of Target Cell Destruct. Mediated by Cytotoxic T-cell Lines, Lymphotoxin-Secreting Helper T-cell Clones, and Cell-Free Lymphotoxin-Containing Supernatant." *PNAS USA*. 83:1881-1885 (1986).

Schneider et al., "BAFF, A Novel Ligand of the Tumor Necrosis Factor Family, Stimulates B Cell Growth" *Journal of Experimental Medicine* 189:1747-1756 (1999).

Schneider et al., "Characterization of Two Receptors for TRAIL." *FEBS Letters*. 416:329-334 (1997).

Screaton et al., "LARD: A New Lymphoid-Specific Death Domain Containing Receptor Regulated by Alternative Pre-mRNA Splicing." *Proc. Natl. Acad. Sci*. 94:4615-4619 (1997).

Screaton et al., "TRICK2, A New Alternatively Spliced Receptor that Transduces the Cytotoxic Signal From TRAIL." *Current Biology*. 7:693-696 (1997).

Sheridan et al., "Control of TRAIL-Induced Apoptosis by a Family of Signaling and Decoy Receptors" *Science* 277:818-821 (1997).

Shu et al., "TALL-1 is a Novel Member of the TNF Family that is Down-Regulated by Mitogens." *J. Leukocyte Biol*. 65:680-683 (1999).

Simonet et al., "Osteoprotegerin: A Novel Screted Protein Involved in the Regulation of Bone Density" *Cell* 89:309-319 (1997).

Smith et al., "A Receptor for Tumor Necrosis Factor Defines an Unusual Family of Cellular and Viral Proteins" *Science* 248:1019-1023 (1990).

Smith et al., "T2 Open Reading Frame From the Shope Fibroma Virus Encodes a Soluble Form of the TNF Receptor." *Biochem. & Biophys. Res. Comm*. 176:335-342 (1991).

Song et al., "Tumor Necrosis Factor-related Apoptosis-inducing Ligand (TRAIL) Is an Inhibitor of Autoimmune Inflammation and Cell Cycle Progression" *Journal of Experimental Medicine* 191(7):1095-1103 (2000).

Stamenkovic et al., "A B-Lymphocyte Activation Molecule Related to the Nerve Growth Factor Receptor and Induced by Cytokines in Carcinomas." *EMBO Journal*. 8(5):1403-1410 (1989).

Tewari and Dixit, "Recent Advances in Tumor Necrosis Factor and CD40 Signaling" *Curr. Op. Genet. Develop*. 6:39-44 (1996).

Thomas and Hersey, "TNF-Related Apoptosis-Inducing Ligand (TRAIL) Induces Apoptosis in Fas Ligand-Resistant Melanoma Cells and Mediates CD4 T Cell Killing of Target Cells" *J. Immunol*. 161:2195-2200 (1998).

Upton et al., "Myxoma Virus Expresses a Secreted Protein with Homology to the Tumor Necrosis Factor Receptor Gene Family that Contributes to Viral Virulence." *Virology*. 184:370-382 (1991).

Upton et al., "Tumorigenic Poxviruses: Genomic Organization and DNA Sequence of the Telomeric Region of the Shope Fibroma Virus Genoma." *Virology*. 160:20-30 (1987).

Verma et al., "Rel/NF-κB/YκB Family: Intimate Tales of Association and Dissociation" *Genes Develop.* 9:2723-2735 (1995).

von Bulow and Bram, "NF-AT Activation Induced by a CAML-Interacting Member of the Tumor Necrosis Factor Receptor Superfamily" *Science* 278:138-141 (1997).

Walczak et al., "TRAIL-R2: A Novel Apoptosis-Mediating Receptor for TRAIL." *EMBO Journal.* 16(17):5386-5397 (1997).

Walczak et al., "Tumoricidal activity of tumor necrosis factor-related apoptosis-inducing ligand in vivo" *Nature Med.* 5:157-163 (1999).

Wiley et al., "Identification and Characterization of a New Member of the TNF Family that Induces Apoptosis" *Immunity* 3:673-682 (1995).

Wong et al., "TRANCE (Tumor Necrosis Factor [TNF]-Related Activation-Induced Cytokine). A New TNF Family Member Predominantly Expressed in T Cells, Is a Dendritic Cell-Specific Survival Factor." *Journal of Experimental Medicine* 186:2075-2080 (1997).

Wong et al., "TRANCE is a TNF Family Member That Regulates Dendritic Cell and Osteoclast Function." *J. Leukocyte Bio.* 65:715-724 (Jun. 1999).

Wu et al., "Killer/DR5 is a DNA Damage-Inducible p53-Regulated Death Receptor Gene." *Nature Genetics.* 17:141-143 (1997).

Yasuda et al., "Identity of Osteoclastogenesis Inhibitory Factor (OCIF) and Osteoprotegerin (OPG): A Mechanism by which OPG/OCIF Inhibits Osteoclastogenesis In Vitro." *Endocrinology.* 139:1329-1337 (1998).

Yonehara et al., "A Cell-Killing Monoclonal Antibody (Anti-Fas) to a Cell Surface Antigen Co-Downregulated with the Receptor of Tumor Necrosis Factor." *Journal of Experimental Medicine* 169:1747-1756 (1989).

Yu et al., "Tumor Necrosis Factor-related Apoptosis-inducing Ligand-mediated Apoptosis in Androgen-independent Prostate Cancer Cells" *Cancer Research* 60:2384-2389 (2000).

Yun et al., "OPG/FDCR-1, A TNF Receptor Family Member, Is Expressed in Lymphoid Cells and Is Up-Regulated by Ligating CD40." *J. Immunol.* 161:6113-6121 (1998).

Zheng et al., "Induction of Apoptosis in Mature T Cells by Tumor Necrosis Factor" *Nature* 377:348-351 (1995).

\* cited by examiner

```
  1 ATGGCGCCAC CACCAGCTAG AGTACATCTA GGTGCGTTCC TGGCAGTGAC
    TACCGCGGTG GTGGTCGATC TCATGTAGAT CCACGCAAGG ACCGTCACTG
  1 MetAlaProP roProAlaAr gValHisLeu GlyAlaPheL euAlaValTh

51 TCCGAATCCC GGGAGCGCAG CGAGTGGGAC AGAGGCAGCC GCGGCCACAC
    AGGCTTAGGG CCCTCGCGTC GCTCACCCTG TCTCCGTCGG CGCCGGTGTG
    rProAsnPro GlySerAlaA laSerGlyTh rGluAlaAla AlaAlaThrPro

101 CCAGCAAAGT GTGGGGCTCT TCCGCGGGGA GGATTGAACC ACGAGGCGGG
    GGTCGTTTCA CACCCCGAGA AGGCGCCCCT CCTAACTTGG TGCTCCGCCC
 35    SerLysVa lTrpGlySer SerAlaGlyA rgIleGluPr oArgGlyGly

151 GGCCGAGGAG CGCTCCCTAC CTCCATGGGA CAGCACGGAC CCAGTGCCCG
    CCGGCTCCTC GCGAGGGATG GAGGTACCCT GTCGTGCCTG GGTCACGGGC
    GlyArgGlyA laLeuProTh rSerMetGly GlnHisGlyP roSerAlaArg

201 GGCCCGGGCA GGGCGCGCCC CAGGACCCAG GCCGGCGCGG AAGCCAGCC
    CCGGGCCCGT CCCGCGCGGG GTCCTGGGTC CGGCCGCGCC CTTCGGTCGG
 68   AlaArgAla GlyArgAlaP roGlyProAr gProAlaArg GluAlaSerP

251 CTCGGCTCCG GGTCCACAAG ACCTTCAAGT TTGTCGTCGT CGGGGTCCTG
    GAGCCGAGGC CCAGGTGTTC TGGAAGTTCA AACAGCAGCA GCCCCAGGAC
    roArgLeuAr gValHisLys ThrPheLysP heValValVa lGlyValLeu

301 CTGCAGGTCG TACCTAGCTC AGCTGCAACC ATGATCAATC AATTGGCACA
    GACGTCCAGC ATGGATCGAG TCGACGTTGG TAGTTTGAAG TACTAGTTAG
101   LeuGlnValV alProSerSe rAlaAlaThr IleLysLeuH isAspGlnSe

351 AATTGGCACA CAGCAATGGG AACATAGCCC TTTGGGAGAG TTGTGTCCAC
    TTAACCGTGT GTCGTTACCC TTGTATCGGG AAACCCTCTC AACACAGGTG
    rIleGlyThr GlnGlnTrpG luHisSerPr oLeuGlyGlu LeuCysProPro

401 CAGGATCTCA TAGATCAGAA CGTCCTGGAG CCTGTAACCG GTGCACAGAG
    GTCCTAGAGT ATCTAGTCTT GCAGGACCTC GGACATTGGC CACGTGTCTC
135    GlySerHi sArgSerGlu ArgProGlyA laCysAsnAr gCysThrGlu

451 GGTGTGGGTT ACACCAATGC TTCCAACAAT TTGTTTGCTT GCCTCCCATG
    CCACACCCAA TGTGGTTACG AAGGTTGTTA AACAAACGAA CGGAGGGTAC
    GlyValGlyT yrThrAsnAl aSerAsnAsn LeuPheAlaC ysLeuProCys

501 TACAGCTTGT AAATCAGATG AAGAAGAGAG AAGTCCCTGC ACCACGACCA
    ATGTCGAACA TTTAGTCTAC TTCTTCTCTC TTCAGGGACG TGGTGCTGGT
168   ThrAlaCys LysSerAspG luGluGluAr gSerProCys ThrThrThrA

551 GGAACACAGC ATGTCAGTGC AAACCAGGAA CTTTCCGGAA TGACAATTCT
    CCTTGTGTCG TACAGTCACG TTTGGTCCTT GAAAGGCCTT ACTGTTAAGA
    rgAsnThrAl aCysGlnCys LysProGlyT hrPheArgAs nAspAsnSer

601 GCTGAGATGT GCCGGAAGTG CAGCACAGGG TGCCCCAGAG GGATGGTCAA
    CGACTCTACA CGGCCTTCAC GTCGTGTCCC ACGGGGTCTC CCTACCAGTT
201   AlaGluMetC ysArgLysCy sSerThrGly CysProArgG lyMetValLy

651 GGTCAAGGAT TGTACGCCCT GGAGTGACAT CGAGTGTGTC CACAAAGAAT
    CCAGTTCCTA ACATGCGGGA CCTCACTGTA GCTCACACAG GTGTTTCTTA
    sValLysAsp CysThrProT rpSerAspIl eGluCysVal HisLysGluSer
```

FIG. 1A

```
701 CAGGCAATGG ACATAATATA TGGGTGATTT TGGTTGTGAC TTTGGTTGTT
    GTCCGTTACC TGTATTATAT ACCCACTAAA ACCAACACTG AAACCAACAA
235    GlyAsnGl yHisAsnIle TrpValIleL euValValTh rLeuValVal

751 CCGTTGCTGT TGGTGGCTGT GCTGATTGTC TGTTGTTGCA TCGGCTCAGG
    GGCAACGACA ACCACCGACA CGACTAACAG ACAACAACGT AGCCGAGTCC
       ProLeuLeuL euValAlaVa lLeuIleVal CysCysCysI leGlySerGly

801 TTGTGGAGGG GACCCCAAGT GCATGGACAG GGTGTGTTTC TGGCGCTTGG
    AACACCTCCC CTGGGGTTCA CGTACCTGTC CCACACAAAG ACCGCGAACC
268    CysGlyGly AspProLysC ysMetAspAr gValCysPhe TrpArgLeuG

851 GTCTCCTACG AGGGCCTGGG GCTGAGGACA ATGCTCACAA CGAGATTCTG
    CAGAGGATGC TCCCGGACCC CGACTCCTGT TACGAGTGTT GCTCTAAGAC
       lyLeuLeuAr gGlyProGly AlaGluAspA snAlaHisAs nGluIleLeu

901 AGCAACGCAG ACTCGCTGTC CACTTTCGTC TCTGAGCAGC AAATGGAAAG
    TCGTTGCGTC TGAGCGACAG GTGAAAGCAG AGACTCGTCG TTTACCTTTC
301 SerAsnAlaA spSerLeuSe rThrPheVal SerGluGlnG lnMetGluSe

951 CCAGGAGCCG GCAGATTTGA CAGGTGTCAC TGTACAGTCC CCAGGGGAGG
    GGTCCTCGGC CGTCTAAACT GTCCACATGT ACATGTCAGG GGTCCCCTCC
       rGlnGluPro AlaAspLeuT hrGlyValTh rValGlnSer ProGlyGluAla

1001 CACAGTGTCT GCTGGGACCG GCAGAAGCTG AAGGGTCTCA GAGGAGGAGG
     GTGTCACAGA CGACCCTGGC CGTCTTCGAC TTCCCAGAGT CTCCTCCTCC
335     GlnCysLe uLeuGlyPro AlaGluAlaG luGlySerGl nArgArgArg

1051 CTGCTGGTTC CAGCAAATGG TGCTGACCCC ACTGAGACTC TGATGCTGTT
     GACGACCAAG GTCGTTTACC ACGACTGGGG TGACTCTGAG ACTACGACAA
        LeuLeuValP roAlaAsnGl yAlaAspPro ThrGluThrL euMetLeuPhe

1101 CTTTGACAAG TTTGCAAACA TCGTGCCCTT TGACTCCTGG GACCAGCTCA
     GAAACTGTTC AAACGTTTGT AGCACGGGAA ACTGAGGACC CTGGTCGAGT
368     PheAspLys PheAlaAsnI leValProPh eAspSerTrp AspGlnLeuM

1151 TGAGGCAGCT GGACCTCACG AAAAATGAGA TCGATGTGGT CAGAGCTGGT
     ACTCCGTCGA CCTGGAGTGC TTTTTACTCT AGCTACACCA GTCTCGACCA
        etArgGlnLe uAspLeuThr LysAsnGluI leAspValVa lArgAlaGly

1201 ACAGCAGGCC CAGGGGATGC CTTGTATGCA ATGCTGATGA AATGGGTCAA
     TGTCGTCCGG GTCCCCTACG GAACATACGT TACGACTACT TTACCCAGTT
401     ThrAlaGlyP roGlyAspAl aLeuTyrAla MetLeuMetL ysTrpValAs

1251 CAAAACTGGA CGGAACGCCT CGATCCACAC CCTGCTGGAT GCCTTGGAGA
     GTTTTGACCT GCCTTGCGGA GCTAGGTGTG GGACGACCTA CGGAACCTCT
        nLysThrGly ArgAsnAlaS erIleHisTh rLeuLeuAsp AlaLeuGluArg

1301 GGATGGAAGA GAGACATGCA AAAGAGAAGA TTCAGGACCT CTTGGTGGAC
     CCTACCTTCT CTCTGTACGT TTTCTCTTCT AAGTCCTGGA GAACCACCTG
435     MetGluGl uArgHisAla LysGluLysI leGlnAspLe uLeuValAsp

1351 TCTGGAAAGT TCATCTACTT AGAAGATGGC ACAGGCTCTG CCGTGTCCTT
     AGACCTTTCA AGTAGATGAA TCTTCTACCG TGTCCGAGAC GGCACAGGAA
        SerGlyLysP heIleTyrLe uGluAspGly ThrGlySerA laValSerLeu

1401 GGAGTGA
     CCTCACT                                    FIG. 1B
468    GluOP*
```

Sera titer of xeno mouse vs DR4 and CD4-IgG

FIG. 3
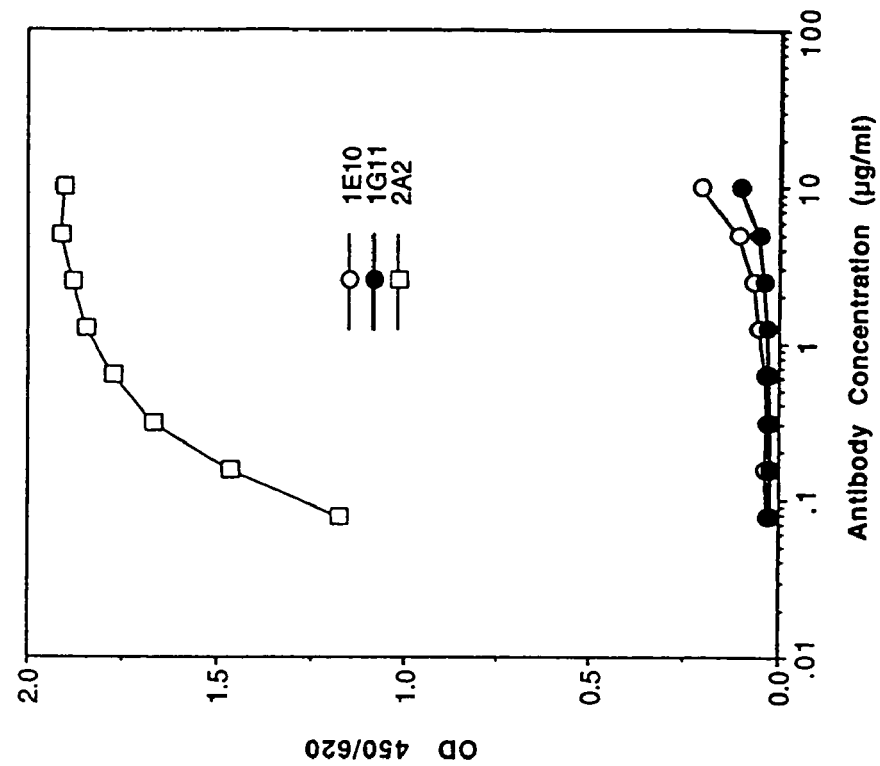
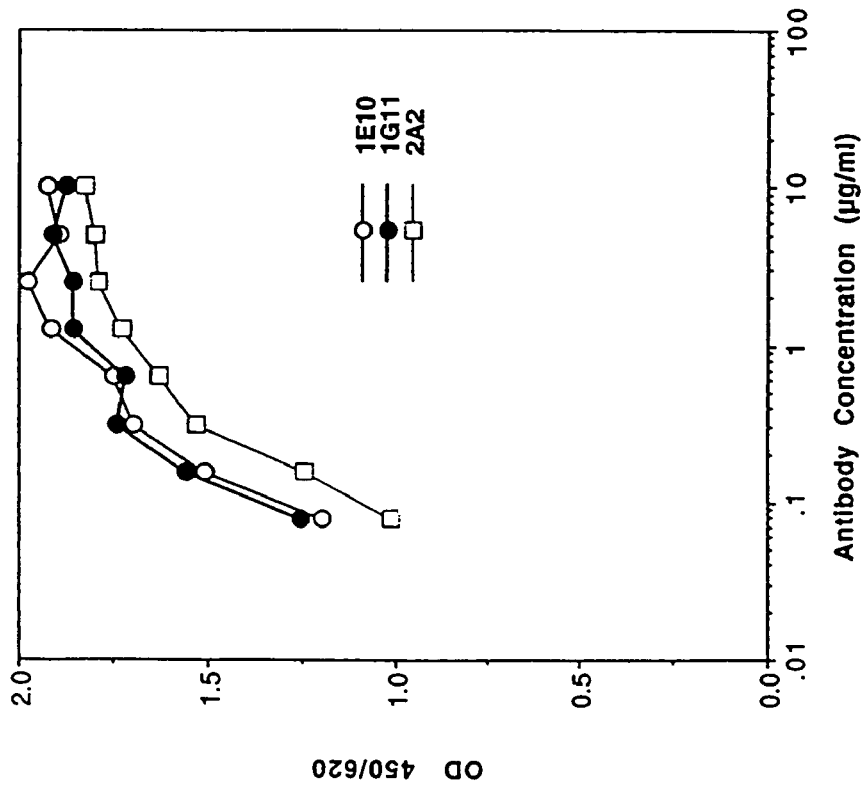

FIG. 5 Apoptosis assay by Annexin V staining

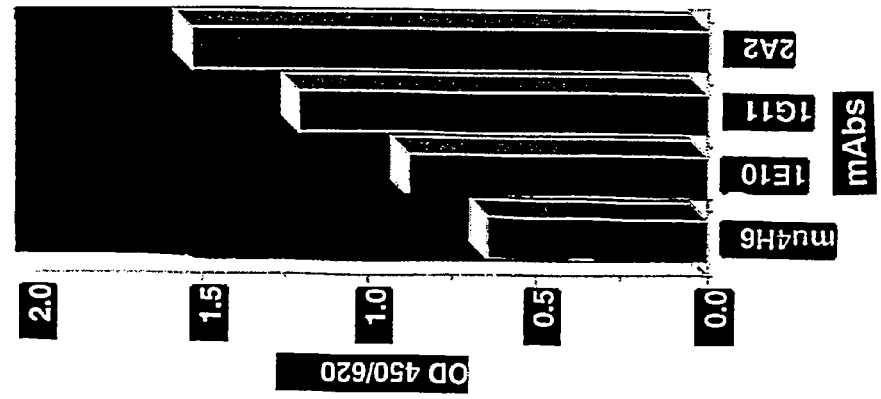
FIG. 7

HUMAN DR4 ANTIBODIES AND USES THEREOF

FIELD OF THE INVENTION

The present invention relates generally to human DR4 antibodies, including antibodies which may be agonistic, antagonistic or blocking antibodies.

BACKGROUND OF THE INVENTION

Various molecules, such as tumor necrosis factor-α ("TNF-α"), tumor necrosis factor-β ("TNF-β" or "lymphotoxin-α"), lymphotoxin-β ("LT-β"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), APRIL, OPG ligand (also referred to as RANK ligand, ODF, or TRANCE), and TALL-1 (also referred to as BlyS, BAFF or THANK) have been identified as members of the tumor necrosis factor ("TNF") family of cytokines [See, e.g., Gruss and Dower, *Blood*, 85:3378-3404 (1995); Schmid et al., *Proc. Natl. Acad. Sci.*, 83:1881 (1986); Dealtry et al., *Eur. J. Immunol.*, 17:689 (1987); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:80-82 (1992), WO 97/01633 published Jan. 16, 1997; WO 97/25428 published Jul. 17, 1997; Marsters et al., *Curr. Biol.*, 8:525-528 (1998); Chicheportiche et al., *Biol. Chem.*, 272:32401-32410 (1997); Hahne et al., *J. Exp. Med.*, 188:1185-1190 (1998); WO98/28426 published Jul. 2, 1998; WO98/46751 published Oct. 22, 1998; WO/98/18921 published May 7, 1998; Moore et al., *Science*, 285:260-263 (1999); Shu et al., *J. Leukocyte Biol.*, 65:680 (1999); Schneider et al., *J. Exp. Med.*, 189:1747-1756 (1999); Mukhopadhyay et al., *J. Biol. Chem.*, 274:15978-15981 (1999)]. Among these molecules, TNF-α, TNF-β, CD30 ligand, 4-1BB ligand, Apo-1 ligand, Apo-2 ligand (Apo2L/TRAIL) and Apo-3 ligand (TWEAK) have been reported to be involved in apoptotic cell death.

Apo2L/TRAIL was identified several years ago as a member of the TNF family of cytokines. [see, e.g., Wiley et al., *Immunity*, 3:673-682 (1995); Pitti et al., *J. Biol. Chem.*, 271:12697-12690 (1996)] The full-length human Apo2L/TRAIL polypeptide is a 281 amino acid long, Type II transmembrane protein. Some cells can produce a natural soluble form of the polypeptide, through enzymatic cleavage of the polypeptide's extracellular region [Mariani et al., *J. Cell. Biol.*, 137:221-229 (1997)] Crystallographic studies of soluble forms of Apo2L/TRAIL reveal a homotrimeric structure similar to the structures of TNF and other related proteins [Hymowitz et al., *Molec. Cell*, 4:563-571 (1999); Hymowitz et al., *Biochemistry*, 39:633-644 (2000)]. Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. [Hymowitz et al., supra; Bodmer et al., *J. Biol. Chem.*, 275:20632-20637 (2000)]

It has been reported in the literature that Apo2L/TRAIL may play a role in immune system modulation, including autoimmune diseases such as rheumatoid arthritis [see, e.g., Thomas et al., *J. Immunol.*, 161:2195-2200 (1998); Johnsen et al., *Cytokine*, 11:664-672 (1999); Griffith et al., *J. Exp. Med.*, 189:1343-1353 (1999); Song et al., *J. Exp. Med.*, 191:1095-1103 (2000)].

Soluble forms of Apo2L/TRAIL have also been reported to induce apoptosis in a variety of cancer cells in vitro, including colon, lung, breast, prostate, bladder, kidney, ovarian and brain tumors, as well as melanoma, leukemia, and multiple myeloma [see, e.g., Wiley et al., supra; Pitti et al., supra; Rieger et al., *FEBS Letters*, 427:124-128 (1998); Ashkenazi et al., *J. Clin. Invest.*, 104:155-162 (1999); Walczak et al., *Nature Med.*, 5:157-163 (1999); Keane et al., *Cancer Research*, 59:734-741 (1999); Mizutani et al., *Clin. Cancer Res.*, 5:2605-2612 (1999); Gazitt, *Leukemia*, 13:1817-1824 (1999); Yu et al., *Cancer Res.*, 60:2384-2389 (2000); Chinnaiyan et al., *Proc. Natl. Acad. Sci.*, 97:1754-1759 (2000)]. In vivo studies in murine tumor models further suggest that Apo2L/TRAIL, alone or in combination with chemotherapy or radiation therapy, can exert substantial anti-tumor effects [see, e.g., Ashkenazi et al., supra; Walzcak et al., supra; Gliniak et al., *Cancer Res.*, 59:6153-6158 (1999); Chinnaiyan et al., supra; Roth et al., *Biochem. Biophys. Res. Comm.*, 265:1999 (1999)]. In contrast to many types of cancer cells, most normal human cell types appear to be resistant to apoptosis induction by certain recombinant forms of Apo2L/TRAIL [Ashkenazi et al., supra; Walzcak et al., supra]. Jo et al. has reported that a polyhistidine-tagged soluble form of Apo2L/TRAIL induced apoptosis in vitro in normal isolated human, but not non-human, hepatocytes [Jo et al., *Nature Med.*, 6:564-567 (2000); see also, Nagata, *Nature Med.*, 6:502-503 (2000)]. It is believed that certain recombinant Apo2L/TRAIL preparations may vary in terms of biochemical properties and biological activities on diseased versus normal cells, depending, for example, on the presence or absence of a tag molecule, zinc content, and % trimer content [See, Lawrence et al., *Nature Med.*, Letter to the Editor, 7:383-385 (2001); Qin et al., *Nature Med.*, Letter to the Editor, 7:385-386 (2001)].

Various molecules in the TNF family also have purported role(s) in the function or development of the immune system [Gruss et al., *Blood*, 85:3378 (1995)]. Zheng et al. have reported that TNF-α is involved in post-stimulation apoptosis of CD8-positive T cells [Zheng et al., *Nature*, 377:348-351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)]. CD40 ligand activates many functions of B cells, including proliferation, immunoglobulin secretion, and survival [Renshaw et al., *J. Exp. Med.*, 180:1889 (1994)]. Another recently identified TNF family cytokine, TALL-1 (BlyS), has been reported, under certain conditions, to induce B cell proliferation and immunoglobulin secretion. [Moore et al., supra; Schneider et al., supra; Mackay et al., *J. Exp. Med.*, 190:1697 (1999)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., *Curr. Op. Immunol.*, 6:279-289 (1994); Nagata et al., *Science*, 267:1449-1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., *J. Exp. Med.*, 169:1747-1756 (1989)].

The TNF-related ligand called OPG ligand (also referred to as RANK ligand, TRANCE, or ODF) has been reported in the literature to have some involvement in certain immunoregulatory activities. WO98/28426 published Jul. 2, 1998 describes the ligand (referred to therein as RANK ligand) as a Type 2 transmembrane protein, which in a soluble form, was found to induce maturation of dendritic cells, enhance CD1a+ dendritic cell allo-stimulatory capacity in a MLR, and enhance the number of viable human peripheral blood T cells in vitro in the presence of TGF-beta. [see also, Anderson et al., *Nature*, 390:175-179 (1997)]. The WO98/28426 reference also discloses that the ligand enhanced production of TNF-alpha by one macrophage tumor cell line (called RAW264.7; ATCC TIB71), but did not stimulate nitric oxide production by those tumor cells.

The putative roles of OPG ligand/TRANCE/ODF in modulating dendritic cell activity [see, e.g., Wong et al., *J. Exp. Med.*, 186:2075-2080 (1997); Wong et al., *J. Leukocyte Biol.*, 65:715-724 (1999); Josien et al., *J. Immunol.*, 162: 2562-2568 (1999); Josien et al., *J. Exp. Med.*, 191495-501 (2000)] and in influencing T cell activation in an immune response [see, e.g., Bachmann et al., *J. Exp. Med.*, 189:1025-1031 (1999); Green et al., *J. Exp. Med.*, 189:1017-1020 (1999)] have been explored in the literature. Kong et al., *Nature*, 397:315-323 (1999) report that mice with a disrupted opgl gene showed severe osteoporosis, lacked osteoclasts, and exhibited defects in early differentiation of T and B lymphocytes. Kong et al. have further reported that systemic activation of T cells in vivo led to an OPGL-mediated increase in osteoclastogenesis and bone loss. [Kong et al., *Nature*, 402:304-308 (1999)].

Induction of various cellular responses mediated by such TNF family cytokines is believed to be initiated by their binding to specific cell receptors. Previously, two distinct TNF receptors of approximately 55-kDa (TNFR1) and 75-kDa (TNFR2) were identified [Hohman et al., *J. Biol. Chem.*, 264:14927-14934 (1989); Brockhaus et al., *Proc. Natl. Acad. Sci.*, 87:3127-3131 (1990); EP 417,563, published Mar. 20, 1991; Loetscher et al., *Cell*, 61:351 (1990); Schall et al., *Cell*, 61:361 (1990); Smith et al., *Science*, 248:1019-1023 (1990); Lewis et al., *Proc. Natl. Acad. Sci.*, 88:2830-2834 (1991); Goodwin et al., *Mol. Cell. Biol.*, 11:3020-3026 (1991)]. Those TNFRs were found to share the typical structure of cell surface receptors including extracellular, transmembrane and intracellular regions. The extracellular portions of both receptors were found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990); Hale et al., *J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. [Schall et al., supra; Loetscher et al., supra; Smith et al., supra; Nophar et al., supra; Kohno et al., supra; Banner et al., *Cell*, 73:431-435 (1993)]. A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., supra and Itoh et al., *Cell*, 66:233-243 (1991)]. CRDs are also found in the soluble TNFR (sTNFR)-like T2 proteins of the Shope and myxoma poxviruses [Upton et al., *Virology*, 160:20-29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily.

The TNF family ligands identified to date, with the exception of lymphotoxin-α, are typically type II transmembrane proteins, whose C-terminus is extracellular. In contrast, most receptors in the TNF receptor (TNFR) family identified to date are typically type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

The TNFR family member, referred to as RANK, has been identified as a receptor for OPG ligand (see WO98/28426 published Jul. 2, 1998; Anderson et al., *Nature*, 390:175-179 (1997); Lacey et al., *Cell*, 93:165-176 (1998). Another TNFR-related molecule, called OPG (FDCR-1 or OCIF), has also been identified as a receptor for OPG ligand. [Simonet et al., *Cell*, 89:309 (1997); Yasuda et al., *Endocrinology*, 139:1329 (1998); Yun et al., *J. Immunol.*, 161: 6113-6121 (1998)]. Yun et al., supra, disclose that OPG/FDCR-1/OCIF is expressed in both a membrane-bound form and a secreted form and has a restricted expression pattern in cells of the immune system, including dendritic cells, EBV-transformed B cell lines and tonsillar B cells. Yun et al. also disclose that in B cells and dendritic cells, expression of OPG/FDCR-1/OCIF can be up-regulated by CD40, a molecule involved in B cell activation. However, Yun et al. acknowledge that how OPG/FDCR-1/OCIF functions in the regulation of the immune response is unknown.

More recently, other members of the TNFR family have been identified. In von Bulow et al., *Science*, 278:138-141 (1997), investigators describe a plasma membrane receptor referred to as Transmembrane Activator and CAML-Interactor or "TACI". The TACI receptor is reported to contain a cysteine-rich motif characteristic of the TNFR family. In an in vitro assay, cross linking of TACI on the surface of transfected Jurkat cells with TACI-specific antibodies led to activation of NF-κB. [see also, WO 98/39361 published Sep. 18, 1998].

Laabi et al., *EMBO J.*, 11:3897-3904 (1992) reported identifying a new gene called "BCM" whose expression was found to coincide with B cell terminal maturation. The open reading frame of the BCM normal cDNA predicted a 184 amino acid long polypeptide with a single transmembrane domain. These investigators later termed this gene "BCMA" [Laabi et al., *Nucleic Acids Res.*, 22:1147-1154 (1994)]. BCMA mRNA expression was reported to be absent in human malignant B cell lines which represent the pro-B lymphocyte stage, and thus, is believed to be linked to the stage of differentiation of lymphocytes [Gras et al., *Int. Immunology*, 7:1093-1106 (1995)]. In Madry et al., *Int. Immunology*, 10:1693-1702 (1998), the cloning of murine BCMA cDNA was described. The murine BCMA cDNA is reported to encode a 185 amino acid long polypeptide having 62% identity to the human BCMA polypeptide. Alignment of the murine and human BCMA protein sequences revealed a conserved motif of six cysteines in the N-terminal region, suggesting that the BCMA protein belongs to the TNFR superfamily [Madry et al., supra].

In Marsters et al., *Curr. Biol.*, 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., *Curr. Biol.*, 6:1669 (1996)]. Apo-3 has also been referred to by other investigators as DR3, wsl-1, TRAMP, and LARD [Chinnaiyan et al., *Science*, 274:990 (1996); Kitson et al., *Nature*, 384:372 (1996); Bodmer et al., *Immunity*, 6:79 (1997); Screaton et al., *Proc. Natl. Acad. Sci.*, 94:4615-4619 (1997)].

Pan et al. have disclosed another TNF receptor family member referred to as "DR4" [Pan et al., *Science*, 276:111-113 (1997); see also WO98/32856 published Jul. 30, 1998]. The DR4 was reported to contain a cytoplasmic death domain capable of engaging the cell suicide apparatus. Pan et al. disclose that DR4 is believed to be a receptor for the ligand known as Apo2L/TRAIL.

In Sheridan et al., *Science*, 277:818-821 (1997) and Pan et al., *Science*, 277:815-818 (1997), another molecule believed to be a receptor for Apo2L/TRAIL is described [see also, WO98/51793 published Nov. 19, 1998; WO98/41629 published Sep. 24, 1998]. That molecule is referred to as DR5 (it has also been alternatively referred to as Apo-2; TRAIL-R, TR6, Tango-63, hAPO8, TRICK2 or KILLER [Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999]. Like DR4, DR5 is reported to contain a cytoplasmic death domain and be capable of signaling apoptosis. The crystal structure of the complex formed between Apo-2L/TRAIL and DR5 is described in Hymowitz et al., *Molecular Cell*, 4:563-571 (1999).

Yet another death domain-containing receptor, DR6, was recently identified [Pan et al., *FEBS Letters*, 431:351-356 (1998)]. Aside from containing four putative extracellular cysteine rich domains and a cytoplasmic death domain, DR6 is believed to contain a putative leucine-zipper sequence that overlaps with a proline-rich motif in the cytoplasmic region. The proline-rich motif resembles sequences that bind to src-homology-3 domains, which are found in many intracellular signal-transducing molecules. In contrast to other death domain-containing receptors referred to above, DR6 does not induce cell death in the apoptosis sensitive indicator cell line, MCF-7, suggesting an alternate function for this receptor. Consistent with this observation, DR6 is presently believed not to associate with death-domain containing adapter molecules, such as FADD, RAIDD and RIP, that mediate downstream signaling from activated death receptors [Pan et al., *FEBS Lett.*, 431:351 (1998)].

A further group of recently identified receptors are referred to as "decoy receptors," which are believed to function as inhibitors, rather than transducers of signaling. This group includes DCR1 (also referred to as TRID, LIT or TRAIL-R3) [Pan et al., *Science*, 276:111-113 (1997); Sheridan et al., *Science*, 277:818-821 (1997); McFarlane et al., *J. Biol. Chem.*, 272:25417-25420 (1997); Schneider et al., *FEBS Letters*, 416:329-334 (1997); Degli-Esposti et al., *J. Exp. Med.*, 186:1165-1170 (1997); and Mongkolsapaya et al., *J. Immunol.*, 160:3-6 (1998)] and DCR2 (also called TRUNDD or TRAIL-R4) [Marsters et al., *Curr. Biol.*, 7:1003-1006 (1997); Pan et al., *FEBS Letters*, 424:41-45 (1998); Degli-Esposti et al., *Immunity*, 7:813-820 (1997)], both cell surface molecules, as well as OPG [Simonet et al., supra; Emery et al., infra] and DCR3 [Pitti et al., *Nature*, 396:699-703 (1998)], both of which are secreted, soluble proteins.

Additional newly identified members of the TNFR family include CAR1, HVEM, GITR, ZTNFR-5, NTR-1, and TNFL1 [Brojatsch et al., *Cell*, 87:845-855 (1996); Montgomery et al., *Cell*, 87:427-436 (1996); Marsters et al., *J. Biol. Chem.*, 272:14029-14032 (1997); Nocentini et al., *Proc. Natl. Acad. Sci. USA* 94:6216-6221 (1997); Emery et al., *J. Biol. Chem.*, 273:14363-14367 (1998); WO99/04001 published Jan. 28, 1999; WO99/07738 published Feb. 18, 1999; WO99/33980 published Jul. 8, 1999].

As reviewed recently by Tewari et al., TNFR1, TNFR2 and CD40 modulate the expression of proinflammatory and costimulatory cytokines, cytokine receptors, and cell adhesion molecules through activation of the transcription factor, NF-κB [Tewari et al., *Curr. Op. Genet. Develop.*, 6:39-44 (1996)]. NF-κB is the prototype of a family of dimeric transcription factors whose subunits contain conserved Rel regions [Verma et al., *Genes Develop.*, 9:2723-2735 (1996); Baldwin, *Ann. Rev. Immunol.*, 14:649-681 (1996)]. In its latent form, NF-κB is complexed with members of the IκB inhibitor family; upon inactivation of the IκB in response to certain stimuli, released NF-κB translocates to the nucleus where it binds to specific DNA sequences and activates gene transcription. As described above, the TNFR members identified to date either include or lack an intracellular death domain region. Some TNFR molecules lacking a death domain, such as TNFR2, CD40, HVEM, and GITR, are capable of modulating NF-κB activity. [see, e.g., Lotz et al., *J. Leukocyte Biol.*, 60:1-7 (1996)].

For a review of the TNF family of cytokines and their receptors, see Ashkenazi and Dixit, *Science*, 281:1305-1308 (1998); Golstein, *Curr. Biol.*, 7:750-753 (1997); Gruss and Dower, supra, Nagata, *Cell*, 88:355-365 (1997); and Locksley et al., *Cell*, 104:487-501 (2001).

SUMMARY OF THE INVENTION

The invention provides human DR4 antibodies which are capable of specifically binding to human DR4 and/or are capable of modulating biological activities associated with DR4 and/or its ligand(s), in particular, apoptosis, and thus are useful in the treatment of various diseases and pathological conditions, including cancer or immune related diseases.

The invention disclosed herein has a number of embodiments. A typical embodiment of the invention is an isolated anti-DR4 antibody having the same biological characteristics of a monoclonal antibody produced by a hybridoma cell line selected from the group consisting of American Type Culture Collection Accession Numbers: PTA-3359, PTA-3360 and PTA-3361. A related embodiment includes an isolated anti-DR4 receptor monoclonal antibody, comprising an antibody which binds to DR4 receptor comprising amino acids 1 to 218 of SEQ ID NO:1 and competitively inhibits binding of a monoclonal antibody produced by a hybridoma deposited as PTA-3359, PTA-3360 or PTA-3361 to the DR4 receptor. Other related embodiments of the invention include an anti-DR4 receptor antibody comprising an antibody which binds to the same DR4 receptor epitope to which a monoclonal antibody produced by a hybridoma deposited as PTA-3359, PTA-3360 or PTA-3361 binds. Specific embodiments of the invention include the hybridomas deposited as ATCC PTA-3359, PTA-3360 and PTA-3361. Related specific embodiments of the invention include the monoclonal antibodies produced by the hybridomas deposited as ATCC PTA-3359, PTA-3360 and PTA-3361. Optionally such anti-DR4 receptor antibodies have a binding affinity to the DR4 receptor of least $10^8$ $M^{-1}$ to $10^{12}$ $M^{-1}$. In preferred embodiments, the anti-DR4 receptor antibodies of the invention are human antibodies.

The antibodies disclosed herein have a number of biological properties. In preferred embodiments of the invention, the anti-DR4 receptor antibodies disclosed herein inhibit binding of Apo-2 ligand comprising amino acids 114 to 281 of SEQ ID NO: 3 to DR4 receptor comprising amino acids 1 to 218 of SEQ ID NO:1. Typically the anti-DR4 receptor antibodies of the invention block Apo-2 ligand induced apoptosis in at least one type of mammalian cells. In an optional embodiment, the anti-DR4 receptor antibodies of the invention neutralize the apoptotic activity of Apo-2 ligand comprising amino acids 114-281 of SEQ ID NO:3 in at least one type of mammalian cancer cells. Preferably the mammalian cancer cells are colon or colorectal cancer cells, breast cancer cells, or lung cancer (small cell or non-small cell) cells.

In preferred embodiments of the invention, the anti-DR4 receptor antibodies disclosed herein induce apoptosis in at least one type of mammalian cell. Typically the anti-DR4 receptor antibodies disclosed herein, upon binding to DR4 receptor expressed in or on a mammalian cell, activate one or more molecules selected from the group consisting of caspase 3, caspase 8, caspase 10 and FADD in the cytoplasm of the mammalian cell. Highly preferred embodiments of the invention include an isolated anti-DR4 receptor monoclonal antibody, comprising an antibody which binds to DR4 receptor comprising amino acids 1 to 218 of SEQ ID NO:1, competitively inhibits binding of the monoclonal antibody produced by a hybridoma deposited as ATCC PTA-3359, PTA-3360 or PTA-3361 to the DR4 receptor and induces apoptosis in at least one type of mammalian cell. In representative embodiments, the mammalian cells are cancer cells, typically colon or colorectal cancer, breast cancer cells, or lung (small cell or non-small cell) cancer cells. In a specific embodiment, the mammalian cells are 9D cells.

Another embodiment of the invention is an isolated anti-DR4 receptor monoclonal antibody, comprising an antibody which binds to DR4 receptor comprising amino acids 1 to 218 of SEQ ID NO:1, wherein the antibody competitively inhibits binding of the monoclonal antibody produced by the hybridoma deposited as ATCC PTA-3359, PTA-3360 or PTA-3361 to the DR4 receptor, and wherein the antibody inhibits binding of Apo-2 ligand comprising amino acids 114 to 281 of SEQ ID NO:3 to DR4 receptor comprising amino acids 1 to 218 of SEQ ID NO:1, and further wherein, upon binding to DR4 receptor expressed in or on a mammalian cell, activates one or more molecules selected from the group consisting of caspase 3, caspase 8, caspase 10 and FADD in the cytoplasm of a mammalian cell.

Additional embodiments of the invention include an anti-DR4 receptor antibody disclosed herein which is linked to one or more non-proteinaceous polymers selected from the group consisting of polyethylene glycol, polypropylene glycol, and polyoxyalkylene. In an alternative embodiment, an anti-DR4 receptor antibody disclosed herein is linked to a cytotoxic agent or enzyme. In yet another embodiment, an anti-DR4 receptor antibody disclosed herein is linked to a radioisotope, a fluorescent compound or a chemiluminescent compound. Optionally, an anti-DR4 receptor antibody disclosed herein is glycosylated or alternatively, unglycosylated.

Another embodiment of the invention includes a method of inducing apoptosis in mammalian cells comprising exposing mammalian cells expressing DR4 receptor to a therapeutically effective amount of an isolated anti-DR4 receptor monoclonal antibody, comprising an antibody which binds to DR4 receptor comprising amino acids 1 to 218 of SEQ ID NO:1 and competitively inhibits binding of a monoclonal antibody produced by a hybridoma deposited as PTA-3359, PTA-3360 or PTA-3361 to the DR4 receptor. In such methods the mammalian cells are typically cancer cells. In preferred embodiments, the anti-DR4 receptor antibody used in these methods is a human antibody.

Yet another embodiment of the invention is a method of inducing apoptosis in mammalian cells comprising exposing mammalian cells expressing DR4 receptor to a therapeutically effective amount of an isolated anti-DR4 receptor monoclonal antibody, comprising an antibody which binds to DR4 receptor comprising amino acids 1 to 218 of SEQ ID NO:1, wherein the antibody competitively inhibits binding of a monoclonal antibody produced by one or more of the hybridomas deposited as PTA-3359, PTA-3360 and PTA-3361 to the DR4 receptor.

The invention also provides compositions comprising one or more DR4 antibodies and a carrier, such as a pharmaceutically-acceptable carrier. In one embodiment, such composition may be included in an article of manufacture or kit.

In addition, therapeutic and diagnostic methods for using DR4 antibodies are provided.

BRIEF DESCRIPTION OF THE DRAWINGS

FIGS. 1A-1B show the nucleotide sequence (SEQ ID NO:2) of a cDNA for full length human DR4 and its derived amino acid sequence (SEQ ID NO:1). The respective nucleotide and amino acid sequences for human DR4 are also reported in Pan et al., Science, 276:111 (1997).

FIGS. 3A and 3B are graphs showing the reactivity of the 1E10, 1G11, and 2A2 anti-DR4 antibodies with DR4-IgG and Apo-2-IgG.

FIGS. 7A-7B are bar graphs showing the results of an ELISA evaluating the epitope mapping of 1E10, 1G11 and 2A2 anti-DR4 antibodies to mu4H6.

DETAILED DESCRIPTION OF THE PREFERRED EMBODIMENTS

I. Definitions

Figure 2:
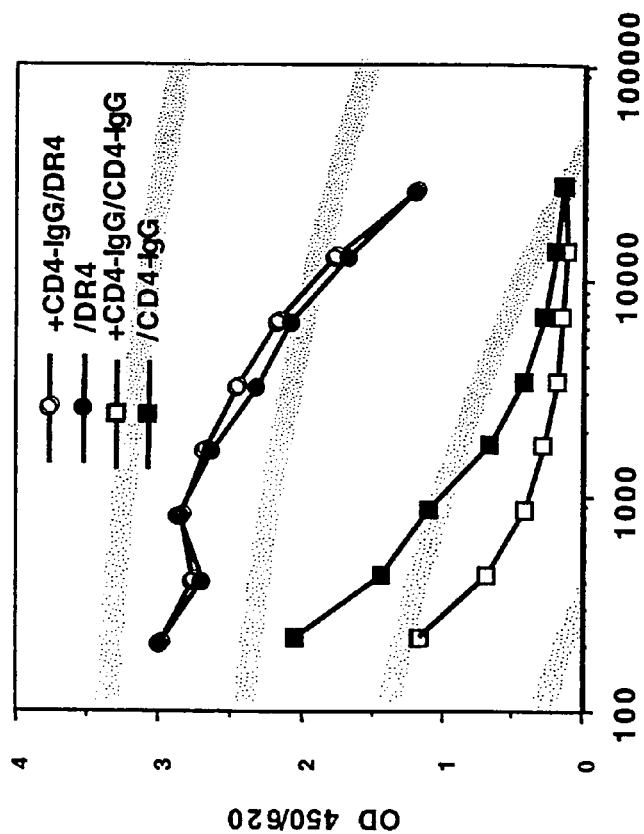
FIG. 2 is a graph showing results of an ELISA testing the titer of endogenous DR4 and CD4-IgG antibodies in xenomouse sera.

As used herein, the term "Apo-2 ligand" or "Apo-2L" (also known as TRAIL) refers to a specific member of the tumor necrosis factor (TNF) ligand family that, among other things, induces apoptosis in a variety of cancer cells [see WO 97/25428 published Jul. 17, 1997; WO97/01633 published Jan. 16, 1997; Pitti et al., *J. Biol. Chem*, 271:12687 (1996); Marsters et al., *Curr. Biol.*, 6:79 (1997); Wiley, S. et al., *Immunity*, 3:637 (1995)]. The term Apo-2L as used herein includes polypeptides disclosed in those references as well as additional fragments and variants thereof which are biologically active in terms of binding to at least one of the DR4, Apo-2 (DR-5), DcR1 or DcR2 receptors or capable of inducing apoptosis in at least one type of mammalian cell. Optionally, for purposes of the biological assays described herein, the Apo-2 ligand is a polypeptide having amino acids 114-211 (SEQ ID NO: 3) and does not include an epitope tag sequence (see, e.g., the Apo-2 ligand described in Ashkenazi et al., *J. Clin. Invest.* 104: 155-162 (1999).

A receptor for Apo-2L has been identified and referred to as DR4, a member of the TNF-receptor family that contains a cytoplasmic "death domain" capable of engaging the cell suicide apparatus [see Pan et al., *Science*, 276:111 (1997)]. DR4 has also been described in WO98/32856 published Jul. 30, 1998. The term "Death Receptor 4" or "DR4" when used herein encompasses native sequence DR4 and DR4 variants (which are further defined herein). These terms encompass DR4 expressed in a variety of mammals, including humans. DR4 may be endogenously expressed as occurs naturally in a variety of human tissue lineages, or may be expressed by recombinant or synthetic methods. A "native sequence DR4" comprises a polypeptide having the same amino acid sequence as a DR4 derived from nature. Thus, a native sequence DR4 can have the amino acid sequence of naturally-occurring DR4 from any mammal. Such native sequence DR4 can be isolated from nature or can be produced by recombinant or synthetic means. The term "native sequence DR4" specifically encompasses naturally-occurring truncated or secreted forms of the DR4 (e.g., a soluble form containing, for instance, an extracellular domain sequence), naturally-occurring variant forms (e.g., alternatively spliced forms) and naturally-occurring allelic variants of the DR4. In one embodiment of the invention, the native sequence DR4 is a mature or full-length native sequence DR4 comprising amino acids 1 to 468 of FIG. 1 (SEQ ID NO:1).

The terms "extracellular domain" or "ECD" herein refer to a form of DR4 which is essentially free of the transmembrane and cytoplasmic domains of DR4. Ordinarily, DR4 ECD will have less than 1% of such transmembrane and/or cytoplasmic domains and preferably, will have less than 0.5% of such domains. Optionally, DR4 ECD will comprise amino acid residues 1 to 218 or residues 24 to 218 of FIG. 1 (SEQ ID NO:1).

"DR4 variant" means a biologically active DR4 having at least about 80% or 85% amino acid sequence identity with the DR4 having the deduced amino acid sequence shown in FIG. 1 (SEQ ID NO:1) for a full-length native sequence or extracellular domain sequence of human DR4. Such DR4 variants include, for instance, DR4 polypeptides wherein one or more amino acid residues are added, or deleted (i.e., fragments), at the N- or C-terminus of the sequence of FIG. 1 (SEQ ID NO:1). Ordinarily, an DR4 variant will have at least about 80% amino acid sequence identity, more preferably at least about 90% amino acid sequence identity, and even more preferably at least about 95% amino acid sequence identity with the amino acid sequence of FIG. 1 (SEQ ID NO:1).

"Percent (%) amino acid sequence identity" with respect to the DR4 sequences (or DR4 antibody sequences) identified herein is defined as the percentage of amino acid residues in a candidate sequence that are identical with the amino acid residues in the DR4 sequence (or DR4 antibody sequence), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN™, Megalign (DNASTAR), or ALIGN-2 (authored by Genentech, Inc. and filed with the U.S. Copyright Office on Dec. 10, 1991). The ALIGN-2 software is publicly available from Genentech, Inc. The ALIGN-2 program should be compiled for use on a UNIX operating system, preferably digital UNIX V4.0D. All sequence comparison parameters are set by the ALIGN-2 program and do not vary. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the DR4 or DR4 antibody natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, are identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" are identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "amino acid" and "amino acids" refer to all naturally occurring L-alpha-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

In the Sequence Listing and Figures, certain other single-letter or three-letter designations may be employed to refer to and identify two or more amino acids or nucleotides at a given position in the sequence.

The terms "agonist" and "agonistic" when used herein refer to or describe a molecule which is capable of, directly or indirectly, substantially inducing, promoting or enhancing DR4 biological activity or activation. Optionally, an "agonist DR4 antibody" is an antibody which has activity comparable to the ligand for DR4, known as Apo-2 ligand (TRAIL), or is capable of activating DR4 receptor which results in an activation of one or more intracellular signalling pathways which may include activation of caspase 3, caspase 8, caspase 10 or FADD.

The terms "antagonist" and "antagonistic" when used herein refer to or describe a molecule which is capable of, directly or indirectly, substantially counteracting, reducing or inhibiting DR4 biological activity or DR4 activation. Optionally, an antagonist is a molecule which neutralizes the biological activity resulting from DR4 activation or formation of a complex between DR4 and its ligand, such as Apo-2 ligand.

The term "antibody" is used in the broadest sense and specifically covers single anti-DR4 monoclonal antibodies (including agonist, antagonist, and neutralizing or blocking antibodies) and anti-DR4 antibody compositions with poly-epitopic specificity. "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic or antagonistic properties described herein.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.*, 186:651-663 (1985); Novotny and Haber, *Proc. Natl. Acad. Sci. USA*, 82:4592-4596 (1985)]. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of an anti-DR4 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552-554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. *Nature Biotechnology*, 14:309-314 (1996): Sheets et al. *PNAS*, (*USA*) 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology*, 10: 779-783 (1992); Lonberg et al., *Nature*, 368: 856-859 (1994); Morrison, *Nature*, 368:812-13 (1994); Fishwild et al., *Nature Biotechnology*, 14: 845-51 (1996); Neuberger, *Nature Biotechnology*, 14: 826 (1996); Lonberg and Huszar, *Intern. Rev. Immunol.*, 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" in one chain thereof and a corresponding introduced "cavity" in the other chain thereof; see U.S. Pat. No. 5,821,333). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.*, 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (*USA*), 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976); and Kim et al., *J. Immunol.*, 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology*, 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene*, 169:147-155 (1995); Yelton et al. *J. Immunol.*, 155:1994-2004 (1995); Jackson et al., *J. Immunol.*, 154(7):3310-9 (1995); and Hawkins et al, *J. Mol. Biol.*, 226:889-896 (1992).

The term "immunospecific" as used in "immunospecific binding of antibodies" for example, refers to the antigen specific binding interaction that occurs between the antigen-combining site of an antibody and the specific antigen recognized by that antibody.

"Biologically active" and "desired biological activity" for the purposes herein mean having the ability to modulate DR4 activity or DR4 activation, including, by way of example, apoptosis (either in an agonistic or stimulating manner or in an antagonistic or blocking manner) in at least one type of mammalian cell in vivo or ex vivo, binding to Apo-2 ligand (TRAIL), or modulating activation of one or more molecules in the intracellular signalling pathway such as caspase 3, caspase 8, caspase 10 or FADD. Assays for determining activation of such intracellular molecules are known in the art, see, e.g., Boldin et al., J. Biol. Chem., 270:7795-7798 (1995); Peter, Cell Death Differ., 7:759-760 (2000); Nagata, Cell, 88:355-365 (1998); Ashkenazi et al., Science, 281:1305-1308 (1999).

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, annexin V binding assays, PARP assays, FACS analysis or DNA electrophoresis, all of which are known in the art. Optionally, apoptotic activity will be determined by way of an annexin V or PARP assay.

The terms "cancer," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, glioma, sarcoma, myeloma (such as multiple myeloma) and leukemia. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

"Autoimmune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, lupus erythematous, thyroiditis, rheumatoid arthritis, psoriasis, multiple sclerosis, autoimmune diabetes, and inflammatory bowel disease (IBD).

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13.

The term "prodrug" as used in this application refers to a precursor or derivative form of a pharmaceutically active substance that is less cytotoxic to cancer cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described below.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $y^{90}$, $Re^{186}$, $Re^{188}$, $Sm^{153}$, $Bi^{212}$, $p^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta^I_1$, see, e.g., Agnew *Chem Intl. Ed. Engl.*, 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The terms "treating," "treatment," and "therapy" as used herein refer to curative therapy, prophylactic therapy, and preventative therapy.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

The term "mammal" as used herein refers to any mammal classified as a mammal, including humans, cows, horses, dogs and cats. In a preferred embodiment of the invention, the mammal is a human.

II. Compositions and Methods of the Invention
  A. DR4 Antibodies

In one embodiment of the invention, DR4 antibodies are provided. Exemplary antibodies include polyclonal, monoclonal, humanized, bispecific, and heteroconjugate antibodies. These antibodies may be agonists, antagonists or blocking antibodies.

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the DR4 polypeptide (or a DR4 ECD) or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in, the art without undue experimentation. The mammal can then be bled, and the serum assayed for DR4 antibody titer. If desired, the mammal can be boosted until the antibody titer increases or plateaus.

2. Monoclonal Antibodies

The antibodies of the invention may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the DR4 polypeptide (or a DR4 ECD) or a fusion protein thereof, such as a DR4 ECD-IgG fusion protein. The immunizing agent may alternatively comprise a fragment or portion of DR4 having one or more amino acids that participate in the binding of Apo-2L to DR4. In a preferred embodiment, the immunizing agent comprises an extracellular domain sequence of DR4 fused to an IgG sequence, such as described in Example 1.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63Ag8U.1, (ATCC CRL 1580) described in Example 2 below. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against DR4. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-DR4 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for DR4 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Iliades et al., *FEBS Letters*, 409:437-441 (1997). Coupling of such single chain fragments using various linkers is described in Kortt et al., *Protein Engineering*, 10:423-433 (1997). A variety of techniques for the recombinant production and manipulation of antibodies are well known in the art. Illustrative examples of such techniques that are typically utilized by skilled artisans are described in greater detail below.

(i) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(ii) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions ($\mu$, $\delta$ and $\chi$), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 (1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

As discussed in detail below, the antibodies of the invention may optionally comprise monomeric, antibodies, dimeric antibodies, as well as multivalent forms of antibodies. Those skilled in the art may construct such dimers or multivalent forms by techniques known in the art and using the DR4 antibodies herein. Methods for preparing monovalent antibodies are also well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

(iii) Bispecific Antibodies

Bispecific antibodies are monoclonal, preferably human or humanized, antibodies that have binding specificities for at least two different antigens. In the present case, one of the binding specificities is for the DR4 receptor, the other one is for any other antigen, and preferably for another receptor or receptor subunit. For example, bispecific antibodies specifically binding a DR4 receptor and another apoptosis/signalling receptor are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., *Methods in Enzymology* 121, 210 (1986).

(iv) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(v) Antibody Fragments

In certain embodiments, the anti-DR4 antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology* 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. A variety of techniques for the production of antibody fragments will be apparent to the skilled practitioner. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

(vi) Amino Acid Sequence Variants of Antibodies

Amino acid sequence variants of the anti-DR4 antibodies are prepared by introducing appropriate nucleotide changes into the anti-DR4 antibody DNA, or by peptide synthesis. Such variants include, for example, deletions from, and/or insertions into and/or substitutions of, residues within the amino acid sequences of the anti-DR4 antibodies of the examples herein. Any combination of deletion, insertion, and substitution is made to arrive at the final construct, provided that the final construct possesses the desired characteristics. The amino acid changes also may alter post-translational processes of the humanized or variant anti-DR4 antibody, such as changing the number or position of glycosylation sites.

A useful method for identification of certain residues or regions of the anti-DR4 antibody that are preferred locations for mutagenesis is called "alanine scanning mutagenesis," as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with DR4 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-DR4 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-DR4 antibody with an N-terminal methionyl residue or the antibody fused to an epitope tag. Other insertional variants of the anti-DR4 antibody molecule include the fusion to the N- or C-terminus of the anti-DR4 antibody of an enzyme or a polypeptide which increases the serum half-life of the antibody (see below).

Another type of variant is an amino acid substitution variant. These variants have at least one amino acid residue in the anti-DR4 antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | Norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | Thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the humanized or variant anti-DR4 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human DR4. Such contact residues and neighboring residues are candidates for substitution according to the techniques elaborated herein. Once such variants are generated, the panel of variants is subjected to screening as described herein and antibodies with superior properties in one or more relevant assays may be selected for further development.

(vii) Glycosylation Variants of Antibodies

Antibodies are glycosylated at conserved positions in their constant regions (Jefferis and Lund, *Chem. Immunol.* 65:111-128 [1997]; Wright and Morrison, *TibTECH* 15:26-32 [1997]). The oligosaccharide side chains of the immunoglobulins affect the protein's function (Boyd et al., *Mol. Immunol.* 32:1311-1318 [1996]; Wittwe and Howard, *Biochem.* 29:4175-4180 [1990]), and the intramolecular interaction between portions of the glycoprotein which can affect the conformation and presented three-dimensional surface of the glycoprotein (Hefferis and Lund, supra; Wyss and Wagner, *Current Opin. Biotech.* 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., *Nature Med.* 1:237-243 (1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., *Mature Biotech.* 17:176-180 [1999]).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc. Glycosylation variants may, for example, be prepared by removing, changing and/or adding one or more glycosylation sites in the nucleic acid sequence encoding the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-DR4 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-DR4 antibody.

The glycosylation (including glycosylation pattern) of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5.278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to, separate oligosaccharides based on charge. Methods for releasing oligosaccharides for analytical purposes are also known, and include, without limitation, enzymatic treatment (commonly performed using peptide-N-glycosidase F/endo-α-galactosidase), elimination using harsh alkaline environment to release mainly O-linked structures, and chemical methods using anhydrous hydrazine to release both N- and O-linked oligosaccharides.

(viii) Exemplary Antibodies

The invention disclosed herein has a number of exemplary embodiments. A variety of the typical embodiments of the invention are described below. The following embodiments are offered for illustrative purposes only, and are not intended to limit the scope of the present invention in any way.

As described in the Examples below, a number of human anti-DR4 monoclonal antibodies have been identified and prepared. Certain of those antibodies referred to as 1G11, 1E10 and 2A2, have been deposited with ATCC (PTA-3361, PTA-3359 and PTA-3360 respectively). In one embodiment, the monoclonal antibodies of the invention will have the same biological characteristics as the monoclonal antibodies secreted by the hybridoma cell line(s) referred to above which have been deposited with ATCC. The term "biological characteristics" is used to refer to the in vitro and/or in vivo activities or properties of the monoclonal antibody, such as the ability to specifically bind to DR4 or to block, induce or enhance DR4 activation (or DR4-related activities). By way of example, a blocking antibody may block binding of Apo-2 ligand to DR4 or block Apo-2 ligand-induced apoptosis in a mammalian cell (such as a cancer cell); optionally such Apo-2 ligand will consist of amino acids 114-281 (SEQ ID NO: 3). As disclosed in the present specification (see e.g. FIGS. 3, 6 and 8), the monoclonal antibody 1G11is characterized as specifically binding to DR4, capable of inducing apoptosis, and capable of blocking Apo-2 ligand binding to DR4. This observation suggests that an anti-DR4 antibody having an epitope which is the same as the Apo-2 ligand binding site on DR4, or alternatively, either overlaps with the Apo-2 ligand binding site on DR4 or creates a steric conformation which prevents Apo-2 ligand from binding DR4, is not essential or required for apoptotic or anti-tumor activity. However, a DR4 antibody having such an epitope or steric conformation may exhibit enhanced efficiency or potency of such apoptotic or anti-tumor activity. The properties and activities of the human DR4 antibodies are further described in the Examples below (and also referred to in Table 2). Optionally, the monoclonal antibodies of the present invention will bind to the same epitope(s) as the 1 G11, 1E10 and 2A2 antibodies disclosed herein. This can be determined by conducting various assays, such as described herein and in the Examples. For instance, to determine whether a monoclonal antibody has the same specificity as the DR4 antibodies specifically referred to herein, one can compare its activity in DR4 blocking assays or apoptosis induction assays, such as those described in the Examples below.

Human, chimeric, hybrid or recombinant anti-DR4 antibodies (as well as, for instance, diabodies or triabodies described herein) may comprise an antibody having full length heavy and light chains or fragments thereof, such as a Fab, Fab', F(ab')$_2$ or Fv fragment, a monomer or dimer of such light chain or heavy chain, a single chain Fv in which such heavy or light chain(s) are joined by a linker molecule, or having variable domains (or hypervariable domains) of such light or heavy chain(s) combined with still other types of antibody domains.

The DR4 antibodies, as described herein, will optionally possess one or more desired biological activities or properties. Such DR4 antibodies may include but are not limited to chimeric, humanized, human, and affinity matured antibodies. As described above, the DR4 antibodies may be constructed or engineered using various techniques to achieve these desired activities or properties. In one embodiment, the DR4 antibody will have a DR4 receptor binding affinity of at least $10^5$ $M^{-1}$, preferably at least in the range of $10^6$ $M^{-1}$ to $10^7$ $M^{-1}$, more preferably, at least in the range of $10^8$ $M^{-1}$ to $10^{12}$ $M^{-1}$ and even more preferably, at least in the range of $10^9$ $M^{-1}$ to $10^{12}$ $M^{-1}$. The binding affinity of the DR4 antibody can be determined without undue experimentation by testing the DR4 antibody in accordance with techniques known in the art, including Scatchard analysis (see Munson et al., supra).

In another embodiment, the DR4 antibody of the invention may bind the same epitope on DR4 to which Apo-2L binds, or bind an epitope on DR4 which coincides or overlaps with the epitope on DR4 to which Apo-2L binds. The DR4 antibody may also interact in such a way to create a steric conformation which prevents Apo-2 ligand binding to DR4. The epitope binding property of a DR4 antibody of the present invention may be determined using techniques known in the art. For instance, the DR4 antibody may be tested in an in vitro assay, such as a competitive inhibition assay, to determine the ability of the DR4 antibody to block or inhibit binding of Apo-2L to DR4. Optionally, the DR4 antibody may be tested in a competitive inhibition assay to determine the ability of the DR4 antibody to inhibit binding of an Apo-2L polypeptide to a DR4-IgG construct or to a cell expressing DR4. Optionally, the DR4 antibody will be capable of blocking or inhibiting binding of Apo-2L to DR4 by at least 50%, preferably by at least 75% and even more preferably by at least 90%, which may be determined, by way of example, in an in vitro competitive inhibition assay using a soluble form of Apo-2 ligand (TRAIL) (such as the 114-281 extracellular domain sequence described in Pitti et al., J. Biol. Chem., supra) and a DR4 ECD-IgG (such as described in Example 1). The epitope binding property of a DR4 antibody may also be determined using in vitro assays to test the ability of the DR4 antibody to block Apo-2L induced apoptosis. Optionally, the DR4 antibody will be capable of blocking or inhibiting Apo-2L induced apoptosis in a selected mammalian cancer cell type by at least 50%, preferably by at least 75% and even more preferably, by at least 90% or 95%, which may be determined, for example, in an in vitro assay.

In a further embodiment, the DR4 antibody will comprise an agonist antibody having activity comparable to Apo-2 ligand (TRAIL). Preferably, such an agonist DR4 antibody will induce apoptosis in at least one type of cancer or tumor cell line or primary tumor. The apoptotic activity of an agonist DR4 antibody may be determined using known in vitro or in vivo assays. Examples of a variety of such in vitro and in vivo assays are well known in the art. In vitro, apoptotic activity can be determined using known techniques such as Annexin V binding. In vivo, apoptotic activity may be determined, e.g., by measuring reduction in tumor burden or volume.

As noted above, the antibodies disclosed herein have a number of properties including the ability to modulate certain physiological interactions and/or processes. As shown in Examples 5 and 7, antibodies disclosed herein are able to induce DR4 mediated apoptosis. In a typical embodiment of the invention, antibodies disclosed herein agonistically induce DR4 mediated apoptosis in 9D cells (a human B lymphoid cell line expressing DR4) as measured by annexin V staining. In a specific embodiment of the invention, the agonistic activity of the antibody is enhanced by crosslinking the antibodies with anti-human IgG Fc. In a preferred embodiment of the invention, this enhanced apoptosis is comparable to the apoptotic activity of Apo-2L in 9D cells. In a highly preferred embodiment, 9D cells exposed to DR4 antibody exhibit a level of apoptosis that is within about 20% and most preferably within about 10% of the level of apoptosis observed in 9D cells exposed to Apo-2L.

As shown in Example 6, antibodies disclosed herein are also able to inhibit the binding of Apo-2 ligand to human DR4. In an illustrative embodiment, antibodies disclosed herein block the binding of biotinylated Apo-2 ligand to human DR4-IgG as measured in an enzyme linked immunoadsorbant assay.

Figure 4:
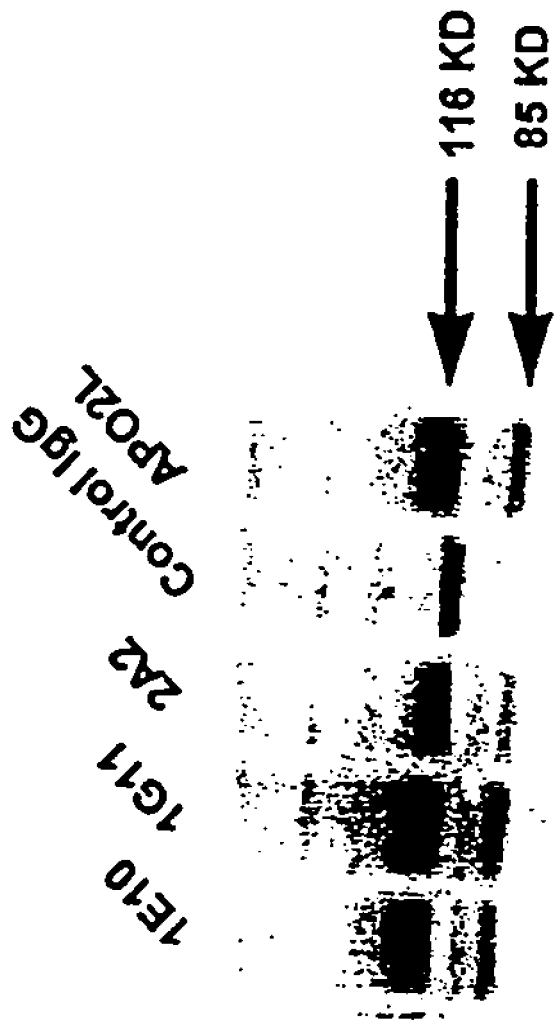
FIG. 4 shows the results of a {poly (ADP-ribose) polymerase} (PARP) assay. In this assay, 9D cells were incubated with 1.0 µg of human anti DR4 and cross linked with anti Human IgG Fc. During apoptosis PARP is cleaved from 116 kD to 85 and 26 kD. The cleavage of PARP is considered to be an early marker of apoptosis.

As observed in the poly ADP-ribose polymerase (PARP) assay shown in Example 8, cells treated with the human DR4 antibodies disclosed herein generate a degraded (85 Kd) PARP. In a typical embodiment of this property that is illustrated in FIG. 4, 9D cells treated with human anti-DR4 antibody and crosslinked with anti-human IgG Fc demonstrate the presence of a cleaved 85 Kd PARP. In highly preferred embodiments of the invention, the relative ratio of intact (116 Kd) PARP to degraded (85 Kd) PARP observed in 9D cells treated with human anti-DR4 antibody cells is comparable to the relative ratio of intact (116 Kd) PARP to degraded (85 Kd) PARP observed in 9D cells treated with Apo-2 ligand (see, e.g. FIG. 4).

The antibodies disclosed herein also exhibit a number of characteristics related to their ability to immunospecifically bind to DR4 epitopes. For example, the antibodies disclosed herein have the ability to bind to specific epitopes on the human DR4 molecule. In addition, antibodies disclosed herein comprise specific amino acid sequences that allow their binding to these human DR4 epitopes. Antibodies disclosed herein also have the ability to competitively inhibit the immunospecific binding of antibodies that recognize an identical or nearly identical epitope on the DR4 molecule. In a typical embodiment illustrated in Example 2, antibody competition for the binding of DR4 epitopes is evaluated in a competition ELISA. In a preferred embodiments of the invention, DR4 epitope binding of a first unlabelled antibody competes with DR4 epitope binding of a second unlabelled antibody. In this embodiment, if the labelled antibody and unlabeled antibody both recognize the same or an overlapping epitope, the unlabelled antibody will compete with the labelled antibody for DR4 epitope binding resulting in a decreased binding of the labelled antibody.

Preferred embodiments of the present invention include DR4 antibodies exhibiting more than one of the physiological and/or immunospecific binding properties disclosed herein. In a typical embodiment, the invention disclosed herein provides an antibody having a first characteristic selected from the group comprising an ability to block the binding of Apo-2 ligand to DR4, an ability to induce apoptosis in 9D cells and an ability to generate a degraded (85 Kd) PARP in a poly ADP-ribose polymerase assay, and in addition exhibit a second characteristic selected from the group comprising the recognition of a specific epitope on the DR4 molecule, the ability to competitively inhibit the immunospecific binding of antibodies that recognize an identical or nearly identical epitope on the DR4 molecule and/or a specific amino acid sequence having at least a portion of the antigen binding site that recognizes the specific epitope on the human DR4 molecule. In highly preferred embodiments, the antibodies disclosed herein exhibit more than one such physiological and/or immunospecific binding properties disclosed herein.

A typical embodiment of the invention is an isolated anti-DR4 antibody having the same biological characteristics of a monoclonal antibody produced by a hybridoma cell line selected from the group consisting of American Type Culture Collection Accession Numbers: PTA-3359, PTA-3360 and PTA-3361. A related embodiment includes an isolated anti-DR4 receptor monoclonal antibody, comprising an antibody which binds to DR4 receptor comprising amino acids 1 to 218 of SEQ ID NO:1 and competitively inhibits binding of a monoclonal antibody produced by a hybridoma deposited as PTA-3359, PTA-3360 or PTA-3361 to the DR4 receptor. Other related embodiments of the invention include an anti-DR4 receptor antibody comprising an antibody which binds to the same DR4 receptor epitope to which a monoclonal antibody produced by a hybridoma deposited as PTA-3359, PTA-3360 or PTA-3361 binds. Specific embodiments of the invention include the hybridomas deposited as ATCC PTA-3359, PTA-3360 and PTA-3361. Related specific embodiments of the invention include the monoclonal antibodies produced by the hybridomas deposited as ATCC PTA-3359, PTA-3360 and PTA-3361. Optionally such anti-DR4 receptor antibodies have a binding affinity to the DR4 receptor of least $10^8$ $M^{-1}$ to $10^{12}$ $M^{-1}$. In preferred embodiments, the anti-DR4 receptor antibodies of the invention are human antibodies.

The antibodies disclosed herein have a number of biological properties. In preferred embodiments of the invention, the anti-DR4 receptor antibodies disclosed herein inhibit binding of Apo-2 ligand comprising amino acids 114 to 281 of SEQ ID NO: 3 to DR4 receptor comprising amino acids 1 to 218 of SEQ ID NO:1. Typically the anti-DR4 receptor antibodies of the invention block Apo-2 ligand induced apoptosis in at least one type of mammalian cells. In a preferred embodiment, the anti-DR4 receptor antibodies of the invention neutralize the apoptotic activity of Apo-2 ligand comprising amino acids 114-281 of SEQ ID NO:3 in at least one type of mammalian cancer cells. Preferably the mammalian cancer cells are colon cells or lung cells.

In preferred embodiments of the invention, the anti-DR4 receptor antibodies disclosed herein induce apoptosis in at least one type of mammalian cell. Typically the anti-DR4 receptor antibodies disclosed herein, upon binding to DR4 receptor expressed in or on a mammalian cell, activate one or more molecules selected from the group consisting of caspase 3, caspase 8, caspase 10 and FADD in the cytoplasm of the mammalian cell. Highly preferred embodiments of the invention include an isolated anti-DR4 receptor monoclonal antibody, comprising an antibody which binds to DR4 receptor comprising amino acids 1 to 218 of SEQ ID NO:1, competitively inhibits binding of the monoclonal antibody produced by a hybridoma deposited as ATCC PTA-3359, PTA-3360 or PTA-3361 to the DR4 receptor and induces apoptosis in at least one type of mammalian cell. In representative embodiments, the mammalian cells are cancer cells, typically colon or lung cancer cells. In a specific embodiment, the mammalian cells are 9D cells.

Another embodiment of the invention is an isolated anti-DR4 receptor monoclonal antibody, comprising an antibody which binds to DR4 receptor comprising amino acids 1 to 218 of SEQ ID NO:1, wherein the antibody competitively inhibits binding of the monoclonal antibody produced by the hybridoma deposited as ATCC PTA-3359, PTA-3360 or PTA-3361 to the DR4 receptor, and wherein the antibody inhibits binding of Apo-2 ligand comprising amino acids 114 to 281 of SEQ ID NO:3 to DR4 receptor comprising amino acids 1 to 218 of SEQ ID NO:1, and further wherein, upon binding to DR4 receptor expressed in or on a mammalian cell, activates one or more molecules selected from the group consisting of caspase 3, caspase 8, caspase 10 and FADD in the cytoplasm of a mammalian cell.

Additional embodiments of the invention include an anti-DR4 receptor antibody disclosed herein which is linked to one or more non-proteinaceous polymers selected from the group consisting of polyethylene glycol, polypropylene glycol, and polyoxyalkylene. In an alternative embodiment, an anti-DR4 receptor antibody disclosed herein which is linked to a cytotoxic agent or enzyme. In yet another embodiment, an anti-DR4 receptor antibody disclosed herein is linked to a radioisotope, a fluorescent compound or a chemiluminescent compound. Optionally, an anti-DR4 receptor antibody disclosed herein is glycosylated or alternatively, unglycosylated.

As discussed in detail below, the antibodies of the invention can be used in a variety of methods of modulating physiological processes. One such embodiment of the invention includes a method of inducing apoptosis in mammalian cells comprising exposing mammalian cells expressing DR4 receptor to a therapeutically effective amount of an isolated anti-DR4 receptor monoclonal antibody, comprising an antibody which binds to DR4 receptor comprising amino acids 1 to 218 of SEQ ID NO:1 and competitively inhibits binding of a monoclonal antibody produced by a hybridoma deposited as PTA-3359, PTA-3360 or PTA-3361 to the DR4 receptor. In such methods the mammalian cells are typically cancer cells. In preferred embodiments, the anti-DR4 receptor antibody used in these methods is a human antibody. Yet another embodiment of the invention is a method of inducing apoptosis in mammalian cells comprising exposing mammalian cells expressing DR4 receptor to a therapeutically effective amount of an isolated anti-DR4 receptor monoclonal antibody, comprising an antibody which binds to DR4 receptor comprising amino acids 1 to 218 of SEQ ID NO:1, wherein the antibody competitively inhibits binding of the monoclonal antibody produced by the hybridomas deposited as PTA-3359, PTA-3360 and PTA-3361 to the DR4 receptor.

3. Triabodies

Triabodies are also within the scope of the invention. Such antibodies are described for instance in Iliades et al., supra and Kortt et al., supra.

4. Other Modifications

Other modifications of the DR4 antibodies are contemplated herein. The antibodies of the present invention may be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 (1984).

Further antibody modifications are contemplated. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The anti-DR4 antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544, 545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent (such as Doxorubicin) is optionally contained within the liposome. See Gabizon et al., *J. National Cancer Inst.* 81 (19):1484 (1989).

The antibodies of the invention include "cross-linked" DR4 antibodies. The term "cross-linked" as used herein refers to binding of at least two IgG molecules together to form one (or single) molecule. The DR4 antibodies may be cross-linked using various linker molecules, preferably the DR4 antibodies are cross-linked using an anti-IgG molecule, complement, chemical modification or molecular engineering. It is appreciated by those skilled in the art that complement has a relatively high affinity to antibody molecules once the antibodies bind to cell surface membrane. Accordingly, it is believed that complement may be used as a cross-linking molecule to link two or more anti-DR4 antibodies bound to cell surface membrane. Cross-linking of the human anti-DR4 antibodies is also described in the Examples using either goat anti-mouse IgG Fc or goat anti-human IgG Fc.

5. Recombinant Methods

The invention also provides isolated nucleic acids encoding DR4 antibodies as disclosed herein, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the antibody). Many vectors are available. The vector components generally include, but are not limited to, one or more of the following: a signal sequence, an origin of replication, one or more marker genes, an enhancer element, a promoter, and a transcription termination sequence.

The methods herein include methods for the production of chimeric or recombinant anti-DR4 antibodies which comprise the steps of providing a vector comprising a DNA sequence encoding an anti-DR4 antibody light chain or heavy chain (or both a light chain and a heavy chain), transfecting or transforming a host cell with the vector, and culturing the host cell(s) under conditions sufficient to produce the recombinant anti-DR4 antibody product.

(i) Signal Sequence Component

The anti-DR4 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding the anti-DR4 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-DR4 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-DR4 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the anti-DR4 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for DR4 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; a human hepatoma line (Hep G2); and myeloma or lymphoma cells (e.g. Y0, J558L, P3 and NSO cells) (see U.S. Pat. No. 5,807,715).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No.

Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX® resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

B. Uses for DR4 Antibodies

The DR4 antibodies of the invention have various utilities. For example, DR4 agonistic antibodies may be employed in methods for treating pathological conditions in mammals such as cancer or immune-related diseases. In the methods, the DR4 antibody, preferably an agonistic antibody, is administered to a mammal, alone or in combination with still other therapeutic agents or techniques.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like. Immune related diseases can also be readily identified. In systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic, sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are Infectious disease including but not limited to viral infection (including but not limited to AIDS, hepatitis A, B, C, D, E) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency), and neoplasia.

The antibody is preferably administered to the mammal in a carrier; preferably a pharmaceutically-acceptable carrier. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., intravenous, intraperitoneal, subcutaneous, intramuscular, intraportal), or by other methods such as infusion that ensure its delivery to the bloodstream in an effective form. The antibody may also be administered by isolated perfusion techniques, such as isolated tissue perfusion, to exert local therapeutic effects. Local or intravenous injection is preferred.

Effective dosages and schedules for administering the antibody may be determined empirically, and making such determinations is within the skill in the art. Those skilled in the art will understand that the dosage of antibody that must be administered will vary depending on, for example, the mammal which will receive the antibody, the route of administration, the particular type of antibody used and other drugs being administered to the mammal. Guidance in selecting appropriate doses for antibody is found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The antibody may also be administered to the mammal in combination with effective amounts of one or more other therapeutic agents. The one or more other therapeutic agents or therapies may include, but are not limited to, chemotherapy (chemotherapeutic agents), radiation therapy, immunoadjuvants, growth inhibitory agents, cytotoxic agents, and cytokines. Other agents known to induce apoptosis in mammalian cells may also be employed, and such agents include TNF-alpha, TNF-beta, CD30 ligand, 4-1BB ligand and Apo-2 ligand, as well as other antibodies which can induce apoptosis. The one or more other therapies may include therapeutic antibodies (other than the DR4 antibody), and such antibodies may include anti-Her receptor antibodies (such as Herceptin™), anti-VEGF antibodies, anti-CD20 antibodies (such as Rituxan®) and antibodies against other receptors for Apo-2 ligand, such as anti-Apo-2 (DR5) antibodies, or antibodies against other TNF receptor family members such as Enbrel®.

Chemotherapies contemplated by the invention include chemical substances or drugs which are known in the art and are commercially available, such as Doxorubicin, 5-Fluorouracil, etoposide, camptothecin, Leucovorin, Cytosine arabinoside, Cyclophosphamide, Thiotepa, Busulfan, Cytoxin, Taxol, Methotrexate, Cisplatin, Melphalan, Vinblastine and Carboplatin. Preparation and dosing schedules for such chemotherapy may be used according to manufacturer's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The chemotherapy is preferably administered in a pharmaceutically-acceptable carrier, such as those described above. The mode of administration of the chemotherapy may be the same as employed for the DR4 antibody or it may be administered to the mammal via a different mode. For example, the DR4 antibody may be injected while the chemotherapy is administered orally to the mammal.

Radiation therapy can be administered to the mammal according to protocols commonly employed in the art and known to the skilled artisan. Such therapy may include cesium, iridium, iodine or cobalt radiation. The radiation therapy may be whole body radiation, or may be directed locally to a specific site or tissue in or on the body. Typically, radiation therapy is administered in pulses over a period of time from about 1 to about 2 weeks. The radiation therapy may, however, be administered over longer periods of time. Optionally, the radiation therapy may be administered as a single dose or as multiple, sequential doses.

The antibody may be administered sequentially or concurrently with the one or more other therapeutic agents. The amounts of antibody and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner.

It is contemplated that the antagonist or blocking DR4 antibodies may also be used in therapy. For example, a DR4 antibody could be administered to a mammal (such as described above) to block DR4 receptor binding to Apo-2L, thus increasing the bioavailability of Apo-2L administered during Apo-2L therapy to induce apoptosis in cancer cells.

The therapeutic effects of the DR4 antibodies of the invention can be examined in in vitro assays and using in vivo animal models. A variety of well known animal models can be used to further understand the role of the DR4 antibodies identified herein in the development and pathogenesis of for instance, immune related disease or cancer, and to test the efficacy of the candidate therapeutic agents. The in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

Animal models, for example, for graft-versus-host disease are known. Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. [Auchincloss, H. Jr. and Sachs, D. H., *Fundamental Immunology*, 2nd ed., W. E. Paul ed., Raven Press, NY, 1989, 889-992]. A suitable procedure is described in detail in Current Protocols in Immuriology, unit 4.4. Other transplant rejection models which can be used to test the compositions of the invention are the allogeneic heart transplant models described by Tanabe, M. et al., *Transplantation*, (1994) 58:23 and Tinubu, S. A. et al., *J. Immunol.*, (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, unit 4.5.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The DR4 antibodies of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., *Immunology*, (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compositions of the invention for activity and effectiveness in the treatment of asthma are described by Wolyniec, W. W. et al., *Am. J. Respir. Cell Mol. Biol.*, (1998) 18:777 and the references cited therein.

Additionally, the DR4 antibodies of the invention can be tested on animal models for psoriasis like diseases. The DR4 antibodies of the invention can be tested in the scid/scid mouse model described by Schon, M. P. et al., *Nat. Med.*, (1997) 3:183, in which the mice demonstrate histopathologic skin lesions resembling psoriasis. Another suitable model is the human skin/scid mouse chimera prepared as described by Nickoloff, B. J. et al., *Am. J. Path.*, (1995) 146:580.

Various animal models are well known for testing anti-cancer activity of a candidate therapeutic composition. These include human tumor xenografting into athymic nude mice or scid/scid mice, or genetic murine tumor models such as p53 knockout mice.

Recombinant (transgenic) animal models can be engineered by introducing the coding portion of the molecules identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA*, 82, 6148-615 [1985]); gene targeting in embryonic stem cells (Thompson et al., *Cell*, 56, 313-321 [1989]); electroporation of embryos (Lo, *Mol. Cel. Biol.*, 3, 1803-1814 [1983]); sperm-mediated gene transfer (Lavitrano et al., *Cell*, 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA*, 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals may be further examined for signs of immune disease pathology, for example by histological examination to determine infiltration of immune cells into specific tissues or for the presence of cancerous or malignant tissue.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

In another embodiment of the invention, methods for employing the antibody in diagnostic assays are provided. For instance, the antibodies may be employed in diagnostic assays to detect expression or overexpression of DR4 in specific cells and tissues. Various diagnostic assay techniques known in the art may be used, such as in vivo imaging assays, in vitro competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014-1021 (1974); Pain et al., *J. Immunol. Meth.*, 40:219-230 (1981); and Nygren, *J. Histochem. and Cytochem.*, 30:407-412 (1982).

DR4 antibodies also are useful for the affinity purification of DR4 from recombinant cell culture or natural sources. In this process, the antibodies against DR4 are immobilized on a suitable support, such a Sephadex resin or filter paper, using methods well known in the art. The immobilized antibody then is contacted with a sample containing the DR4 to be purified, and thereafter the support is washed with a suitable solvent that will remove substantially all the material in the sample except the DR4, which is bound to the immobilized antibody. Finally, the support is washed with another suitable solvent that will release the DR4 from the antibody.

In a further embodiment of the invention, there are provided articles of manufacture and kits containing materials useful for treating pathological conditions or detecting or purifying DR4. The article of manufacture comprises a container with a label. Suitable containers include, for example, bottles, vials, and test tubes. The containers may be formed from a variety of materials such as glass or plastic. The container holds a composition having an active agent which is effective for treating pathological conditions or for detecting or purifying DR4. The active agent in the composition is a DR4 antibody and preferably, comprises monoclonal antibodies specific for DR4. The label on the container indicates that the composition is used for treating pathological conditions or detecting or purifying DR4, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. A number of the reagents and protocols disclosed herein are further discussed in WO 99/37684, WO 00/73349, WO 98/32856 and WO 99/64461, the contents of which are hereby incorporated by reference in their entirety.

Example 1

Expression of DR4 ECD as an Immunoadhesin

A soluble DR4 ECD immunoadhesin construct was prepared. A mature DR4 ECD sequence (amino acids 1-218 shown in FIG. 1) was cloned into a pCMV-1 Flag vector (Kodak) downstream of the Flag signal sequence and fused to the CH1, hinge and Fc region of human immunoglobulin $G_1$ heavy chain as described previously [Aruffo et al., *Cell*, 61:1303-1313 (1990)]. The immunoadhesin was expressed by transient transfection into human 293 cells and purified from cell supernatants by protein A affinity chromatography, as described by Haak-Frendscho et al., *Immunology* 79(4): 594-9, (1993).

Example 2

Production and Characterization of Human anti-DR4 Monoclonal Antibodies

Production of Antibodies

Transgenic mice producing human IgG2 or IgG4 (Xenomice, described in Mendez et al., *Nature Genetics* 15: 146-156 [1997]) were hyperimmunized via the rear footpad with 2 μg of DR4 ECD immunoadhesin protein (described in Example 1) in Ribi adjuvant as described in Mendez et al. (supra). Mice were immunized in this manner twice a week for 5 weeks. FIG. 2 shows the endogenous sera titer of xeno mouse vs DR4 and CD4-IgG.

Three days after the final boost, popliteal lymph nodes were removed from the mice and a single cell suspension was prepared in DMEM media (obtained from Biowhitakker Corp.) supplemented with 1% penicillin-streptomycin. The lymph node cells were then fused with myeloma cells P3X63Ag8U.1 (ATCC CRL 1580) using 35% polyethylene glycol and cultured in 96-well culture plates. The lymph nodes of 5 Xenomice yielded $28 \times 10^6$ cells which were plated out at $1 \times 10^5$ cells/well, with a total of 288 wells. The spleen of Xenomouse #263 (titer 1:20,000) yielded $42 \times 10^6$ cells which were plated out at $2 \times 10^5$ cells/well, with a total of 498 wells. Hybridomas resulting from the fusion were selected in HAT medium. Ten days after the fusion, hybridoma culture supernatants were screened in an ELISA to test for the presence of monoclonal antibodies binding to the DR4 ECD immunoadhesin protein (described in Example 1).

In the ELISA, 96-well microtiter plates (Maxisorp; Nunc, Kamstrup, Denmark) were coated by adding 50 μl of 2 μg/ml DR4-Ig in coating buffer (50 mM Carbonate buffer pH 9.6) to each well and incubating at 4° C. overnight. The plates were then washed three times with wash buffer (PBS containing 0.05% Tween 20). The wells in the microtiter plates were then blocked with 200 μl of 2.0% bovine serum albumin in PBS and incubated at room temperature for 1 hour. The plates were then washed again three times with wash buffer.

Following the wash steps, 100 μl of the hybridoma supernatants or Protein G-sepharose column purified antibody (10 μg/ml) was added to designated wells. 100 μl of myeloma cell conditioned medium was added to other designated wells as controls. The plates were incubated at room temperature for 1 hour on a shaker apparatus and then washed three times with wash buffer.

Next, 50 μl HRP-conjugated goat anti-human kappa chain bound (purchased from Cappel Laboratories), diluted 1:5000 in assay buffer (0.5% bovine serum albumin, 0.05% Tween-20 in PBS), was added to each well and the plates incubated for 1 hour at room temperature on a shaker apparatus. The plates were washed three times with wash buffer, followed by addition of 50 μl of substrate (TMB Microwell Peroxidase Substrate; Kirkegaard & Perry, Gaithersburg, Md.) to each well and incubation at room temperature for 10 minutes. The reaction was stopped by adding 50 μl of TMB 1-Component Stop Solution (Diethyl Glycol; Kirkegaard & Perry) to each well, and absorbance at 450 nm was read in an automated microtiter plate reader.

Hybridoma supernatants initially screened in the ELISA were considered for their ability to bind to DR4-IgG but not to CD4-IgG. The supernatants testing positive in the ELISA were further analyzed by FACS analysis using 9D cells (a human B lymphoid cell line expressing DR4; Genentech, Inc.) and PE-conjugated goat anti-human (H & L) IgG. For this analysis, 25 μl of cells suspended (at $4 \times 10^6$ cells/ml) in cell sorter buffer (PBS containing 1% FCS and 0.02% $NaN_3$) were added to U-bottom microtiter wells, mixed with 100 μl of culture supernatant or purified antibody (10 μg/ml) in cell sorter buffer, and incubated for 30 minutes on ice. The cells were then washed twice, resuspended in 150 μl of cell sorter buffer and then analyzed by FACScan (Becton Dickinson, Mountain View, Calif.).

Hybridomas producing anti-DR4 antibodies were subcloned by limiting dilution and then re-assayed to confirm agonist activity.

Anti-DR4 monoclonal antibodies were generated from the xenomouse fusion and were designated "1E10.16.4" (also referred to herein as "1E10"), "1G11.14.7" (also referred to herein as "1G11") and "2A2.16.7" (also referred to herein as "2A2"). 1E10 and 2A2 antibodies have MOPC light chain contamination. 1G11 is a fully human monoclonal antibody.

To identify and characterize mouse IgG contamination, in an ELISA, 96-well microtiter plates (Maxisorp; Nunc, Kamstrup, Denmark) were coated by adding 100 μl of Goat anti-mouse Kappa light chain (Southern biotechnology, Birmingham, Ala.) diluted 1:640 in Coating Buffer (50 mm Carbonate buffer p 9.6) to each well and incubating at 4° C. overnight. The plates were then washed three times with washing buffer (PBS containing 0.05% Tween 20). The wells were then blocked with 200 μl of 2% bovine serum albumin in PBS and incubated at room temperature for 1 hour. The plates were then washed again three times with wash buffer. Following the wash steps, 100 μl of purified antibody (1.0 μg/ml) in assay buffer (0.5% bovine serum albumin, 0.05% Tween 20 in PBS) was added to designated wells. The plates were incubated at room temperature for 1 hour on a shaker apparatus and then washed three times with wash buffer. Next, 100 μl of HRP-goat anti-human IgG Fc specific (ICN) diluted 1:1000 in assay buffer was added to each well and the plates incubated for 1 hour at room temperature on a shaker. The plates were then washed three times with wash buffer, followed by addition of 5 μl of substrate (TMB Microwell peroxidase substrate, Kirkegaard & Perry, Gaithersburg, Md.) to each well and incubated at room temperature for 10 minutes. Adding 50 μl of TMB-1 component stop solution (Diethyl Glycol; Kirkegaard & Perry, Gaithersburg, Md.) to each well to stop the reaction and absorbance at 450 nm was then read in an automated microtiter plate reader.

A summary of the characteristics of these antibodies is provided in Table 2 below.

TABLE 2

Summary of Human Anti DR4 Antibody Characteristics

| | ELISA DR4 | ELISA Apo-2 ("DR5") | FACS[1] | Apoptosis[2] | PARP Assay[3] | Inhibit Apo2L binding |
|---|---|---|---|---|---|---|
| 1E10.16.4 | + | − | ++ | ++ | ++ | +++ |
| 1G11.14.7 | + | − | ++ | ++ | +++ | ++ |
| 2A2.16.7 | + | + | + | + | + | + |

[1]Cell surface staining on human 9D cells
[2]Apoptosis assay by annexin V staining on 9D cells
[3]Cleavage of PARP of 9D cells Epitope Mapping Competition ELISA A competition ELISA was conducted to examine epitope binding properties of the anti-DR4 antibodies disclosed above. In this assay, DR4-Ig (1 µg/ml) as described in Example 1 was used as a capture antigen to coat microtiter plate. A specific biotinylated anti-DR4 monoclonal antibody (4H6 murine monoclonal antibody @ 1 µg/ml; ATCC HB-12455) was added to the coated plate either alone or in presence of another anti-DR4 monoclonal antibody that was unlabeled and used in excess (50 µg/ml) as compared to the labeled antibody. If biotinylated antibody and unlabeled antibody both recognize the same or overlapping epitope, they will compete for binding to the immobilized DR4, resulting in decreased binding of the labeled antibody. If they recognize different and non-overlapping epitopes, there will be no competition between them, and the binding of the labeled antibody to the immobilized DR4 will not be affected. The results of this assay are shown in FIG. 7.

Example 3

Antibody Isotyping

The isotypes of the human anti-DR4 antibodies (as described above) were determined by coating microtiter plates with isotype specific goat anti-mouse Ig (Fisher Biotech, Pittsburgh, Pa.) and goat anti-human Ig (Cappel, ICN Pharmaceuticals, Costa Mesa Calif.) overnight at 4° C. The plates were then washed with wash buffer (as described in Example 2 above). The wells in the microtiter plates were then blocked with 200 µl of 2% bovine serum albumin and incubated at room temperature for one hour. The plates were washed again three times with wash buffer.

Next, 100 µl of 5 µg/ml of purified DR4 antibodies or 100 µl of the hybridoma culture supernatant was added to designated wells. The plates were incubated at room temperature for 30 minutes and then 50 µl HRP-conjugated goat anti-mouse IgG (as described above) was added to each well. The plates were incubated for 30 minutes at room temperature. The level of HRP bound to the plate was detected using HRP substrate as described above.

The isotyping analysis showed that the 1G11, 1E10 and 2A2 antibodies are human $IgG_2$.

Example 4

ELISA Assay to Test Binding of DR4 Antibodies to Other Apo-2L Receptors

An ELISA was conducted to determine if the DR4 antibodies described in Example 2 were able to bind other known Apo-2L receptors beside DR4. Specifically, the DR4 antibodies were tested for binding to Apo-2 [see, e.g., Sheridan et al., Science, 277:818-821 (1997)]. The ELISA was performed essentially as described in Example 2 above.

The results are shown in FIG. 3.

Example 5

Assay for Ability of DR4 Antibodies to Agonistically Induce Apoptosis

Figure 5:
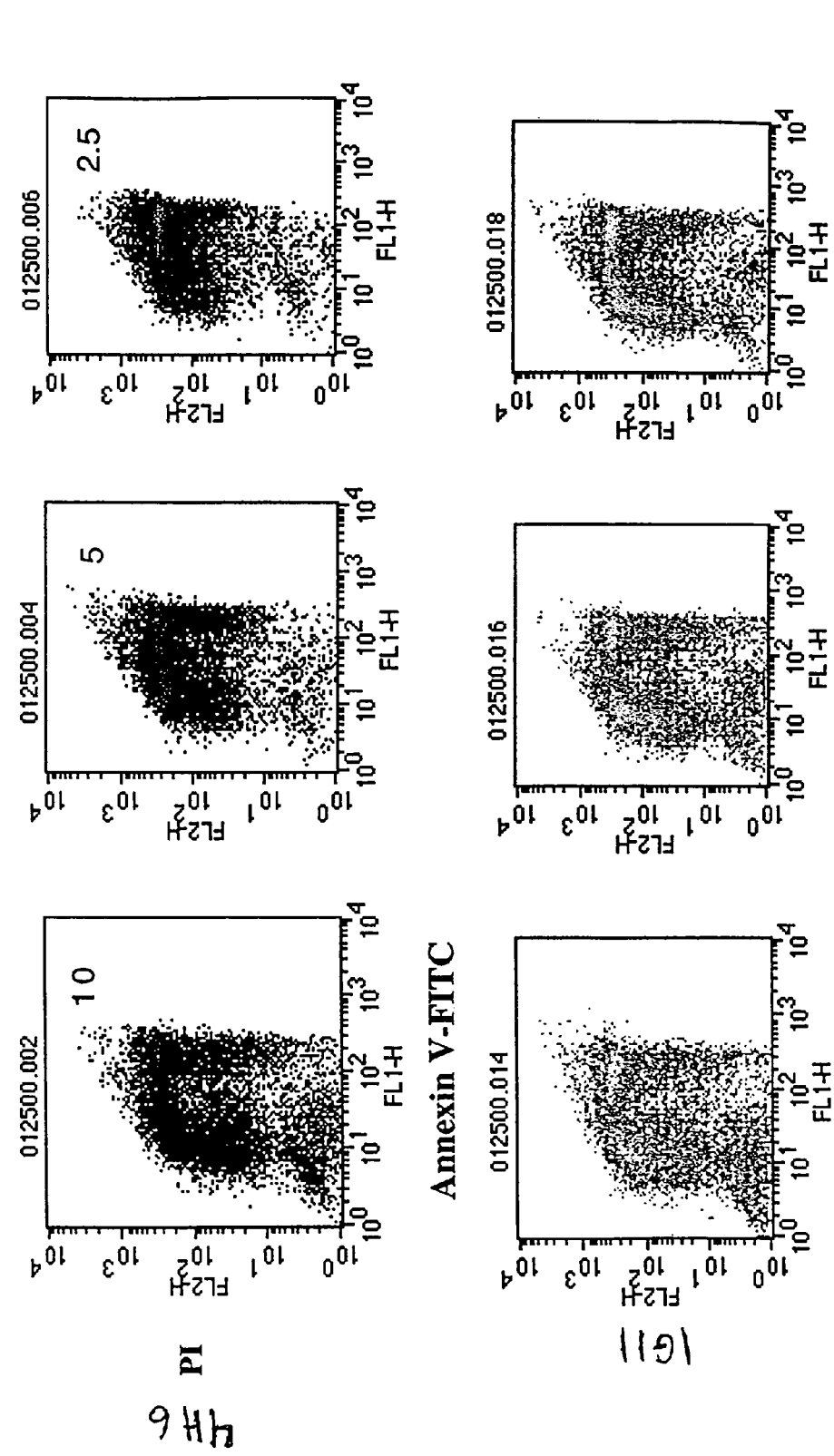
FIGS. 5A-5F show FACS analysis of the 4H6 and 1G11 anti-DR4 antibodies in an apoptosis assay by Annexin V staining.

Hybridoma supernatants and purified antibodies (as described in Example 2 above) were tested for activity to induce DR4 mediated 9D cell apoptosis. Human 9D cells ($5 \times 10^5$) were suspended in 100 microliter complete RPMI medium (RPMI plus 10% FCS, glutamine, nonessential amino acids, penicillin, streptomycin and sodium pyruvate) and added to 24 well macrotiter wells ($5 \times 10^5$ cells/0.5 ml/well). The 9D cells ($5 \times 10^5$ cells/0.5 ml) were incubated with 100 µl of 10 µg/ml purified Mabs(see Example 2 above) or IgG control antibodies in 200 µl complete RPMI media at 4° C. for 15 minutes. The cells were then incubated for 5 minutes at 37° C. with or without 10 µg of goat anti-human IgG Fc antibody (ICN Pharmaceuticals) in 300 µl of complete RPMI. At this point, the cells were incubated for 6 hours at 37° C. and in the presence of 7% $CO_2$. The cells were then harvested and washed once with PBS. The apoptosis of the cells was determined by staining of FITC-annexin V binding to phosphatidylserine according to manufacturer recommendations (Clontech) The cells were washed in PBS and resuspended in 200 µl binding buffer. Ten µl of annexin-V-FITC (1 µg/ml) and 10 µl of propidium iodide were added to the cells. After incubation for 15 minutes in the dark, the 9D cells were analyzed by FACS. FIG. 5 shows an apoptosis assay by annexin V staining.

Figure 6:
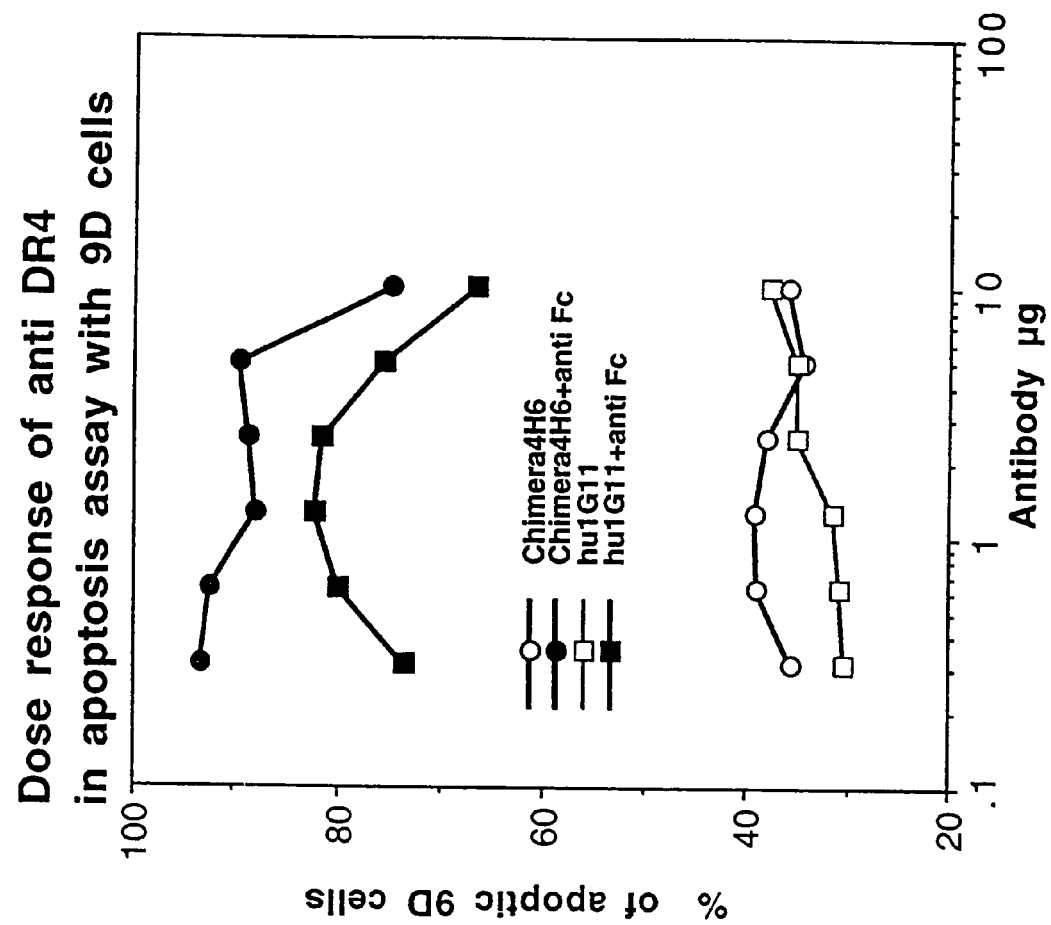
FIG. 6 is a graph showing the induction of apoptosis in 9D cells by varying concentrations of murine 4H6 and huIgG11 anti-DR4 antibodies.

As shown in FIG. 6, DR4 antibody 1G11, induced apoptosis in the 9D cells as compared to the control antibody 4H6. Agonistic activity of 1G11 was enhanced by DR4 receptor cross-linking in the presence of the goat anti-human IgG Fc (FIG. 6). This enhanced apoptosis (FIG. 6) by both DR4 antibodies is comparable to the apoptotic activity of Apo-2L in 9D cells.

Example 6

Assay for DR4 Antibody Ability to Block Binding of Apo-2L to DR4

Purified antibodies (as described in Example 2 above) were tested for activity to block the binding of Apo-2 ligand to DR4. In the ELISA, 96-well microtiter plates (Maxisorp; Nunc, Kamstrup, Denmark) were coated by adding 50 µl of DR4-IgG in Coating Buffer (50 mM Carbonate buffer pH 9.6) to each well and incubating at 4° C. overnight. The plates were then washed three times with washing buffer (PBS containing 0.05% Tween 20). The wells were then blocked with 200 µl of 2% bovine serum albumin in PBS and incubated at room temperature for 1 hour. The plates were then washed again three times with wash buffer.

Following the wash steps, 100 µl of a two-fold serial dilution of purified antibody (50 µg/ml) in assay buffer (0.5% bovine serum albumin, 0.05% Tween 20 in PBS) was added to designated wells. The plates were then incubated at room temperature for 1 hour on a shaker apparatus and washed three times with wash buffer.

Next, 100 µl of Biotinylated Apo-2L diluted 1:1000 in assay buffer was added to each well and the plates incubated for 1 hour at room temperature on a shaker. The plates were then washed three times with wash buffer followed by the addition of 100 µl of Streptavidin-HRP (Zymed, South San Francisco Calif.) diluted 1:1000 in assay buffer and incubated 1 hour at room temperature on a shaker apparatus and then washed three times with wash buffer.

Followed by addition of 50 µl of substrate (TMB Microwell peroxidase substrate, Kirkegaard & Perry, Gaithersburg, Md.) to each well and incubated at room temperature for 10 minutes. 50 µl of TMB-1 component stop solution (Diethyl Glycol; Kirkegaard & Perry, Gaithersburg, Md.) was added to each well to stop the reaction, and absorbance at 450 nm was read in an automated microtiter plate reader.

Figure 8:
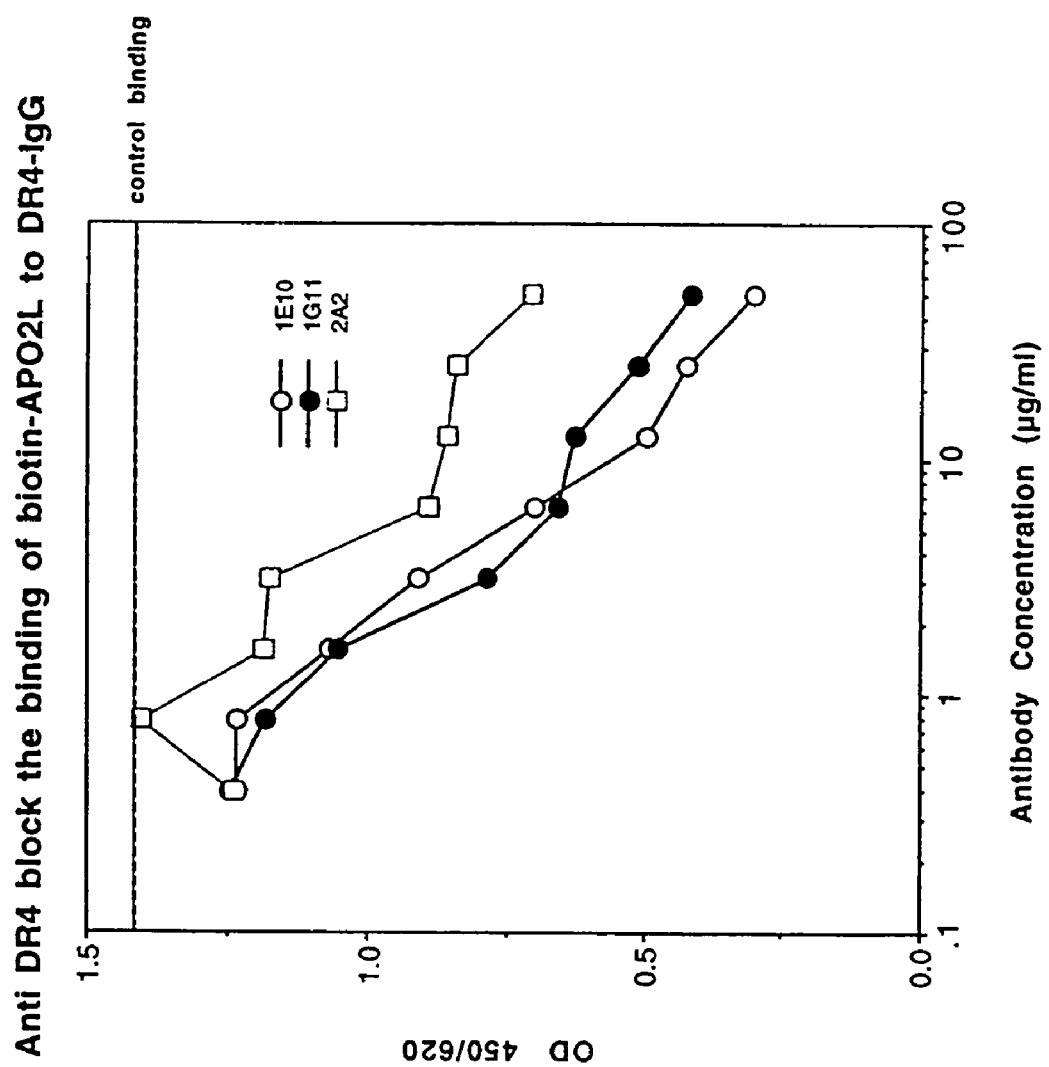
FIG. 8 is a graph showing results of an ELISA testing the ability of DR4 antibodies 1E10, 2A2 and 1G11 to block the binding of biotin-Apo2L to DR4-IgG.

The results are shown in FIG. 8.

Example 7

Apoptosis Assay of 9D Cells Using Cross-linked DR4 Antibodies

The apoptotic activity of cross-linked 1G11 and 4H6 DR4 antibodies on 9D cells was also examined. The 9D cells ($5\times10^5$) were suspended in 100 microliter complete RPMI medium (RPMI plus 10% FCS, glutamine, nonessential amino acids, penicillin, streptomycin and sodium pyruvate) and incubated with 1 microgram of DR4 antibody/100 microliter on ice for 15 minutes. The cells were incubated with 100 microgram/ml of goat anti-human IgG-Fc (Cappel Laboratories) in 300 microliter complete medium overnight at 37° C. in the presence of 7% CO2.

At the end of the incubation, cells were washed once with PBS and suspended in 200 microliter of binding buffer (Clontech). Next, 10 microliter of FITC-Annexin V (Clontech) and 10 microliter of propidium iodide were added to the cells. [See, Moore et al., *Cell Biol.*, 57:265 (1998)]. After incubation for 15 minutes in the dark, the cells were analyzed by FACScan.

The results are shown in FIG. 6. The results show that the 1G11 and 4H6 anti-DR4 antibodies induced apoptosis of 9D cells when cross-linked with anti-Fc IgG. The apoptotic activity of the cross-linked DR4 antibodies (at concentrations of about 1-2 microgram/ml) was comparable to the apoptotic activity of Apo-2L at similar concentrations.

Example 8 poly ADP-ribose polymerase (PARP) Assay

A PARP assay was conducted to determine whether the activity induced by the IgG2 anti-DR4 antibodies was achieved by apoptosis or by conventional complement lysis.

9D cells ($5\times10^5$ cells in 100 µl of complete medium) were incubated with 100 µl of antibody (10 µg/ml) for 15 minutes on ice. Then, 300 µl of goat anti-human IgG Fc (Cappel) was added to the cells. The cells were then incubated overnight at 37° C. At the end of the incubation, the cells were microcentrifuged, harvested and washed once in cell wash buffer (50 mM Tris-HCl, pH 7.5, 0.15 M NaCl, 1 mM $CaCl_2$, 1 mM $MgCl_2$). The cell pellets were then lysed with 50 µl of cell lysis buffer (cell wash buffer plus 1%. NP40) containing protease inhibitors, incubated on ice for 30 minutes, and then spun at 13,000 rpm for 10 minutes.

The cell lysate was mixed with an equal volume of 2×SDS reducing buffer. After boiling 2 minutes, proteins were separated onto a 7.5% SDS PAGE gel and transferred to immunoblot PVDF membranes (Gelman). After blocking the nonspecific binding sites with blocking buffer (Boehringer Mannheim), poly-(ADP-ribose)-polymerase was detected using HRP-rabbit anti-poly(ADP-ribose)-polymerase (Boehringer Mannheim). This antibody will detect the intact (116 Kd) as well as degraded (85 Kd) PARP which is generated as an early step of apoptosis. Bound anti-HRP-rabbit anti-poly-(ADP-ribose)-polymerase was detected using chemiluminescent immunoassay signal reagents according to manufacturer instructions (Amersham, Arlington Heights, Ill.).

The results are shown in FIG. 4. As shown in FIG. 4, cells treated with a number of the human anti-DR4 antibodies and crosslinked with anti-human IgG Fc demonstrated the presence of cleaved 85 Kd PARP, indicating that the mechanism of the 9D cell death induced by the respective antibodies was due to apoptosis.

Example 9

Cell Death Assay Using DR4 mAbs

The effects of several of the DR4 monoclonal antibodies on cell death was examined in human cancer cell lines (SK-MES-1 and H460 lung adenocarcinoma, COLO 205 colon carcinoma, MDA-MB-231 breast carcinoma, and KYM-1 rhabdomyosarcoma). Apo2L was also assayed as a control. Anti-DR4 antibodies (2A2, 1G11, and 1E10) or Apo2L (114-281 amino acids of SEQ ID NO:3) were serially diluted in medium and incubated in the absence or presence of mouse anti-human IgG Fc F(ab')2 fragment (1 µg/mL final concentration) for 30 minutes at 37° C. before addition to the cells. The plates were then incubated at 37° C. for 24 or 48 hours (as indicated on each of FIGS. 9-13). Alamar-Blue was added to the wells for the last 3 to 5 hours of the incubation time. At the end of the incubation period, fluorescence was read using a 96-well fluorometer with excitation at 530 nm and emission of 590 nm. The results are expressed in relative fluorescence units (RFU). For data analysis, a 4-parameter curve fitting program (Kaleidagraph) was used.

Figure 9A:
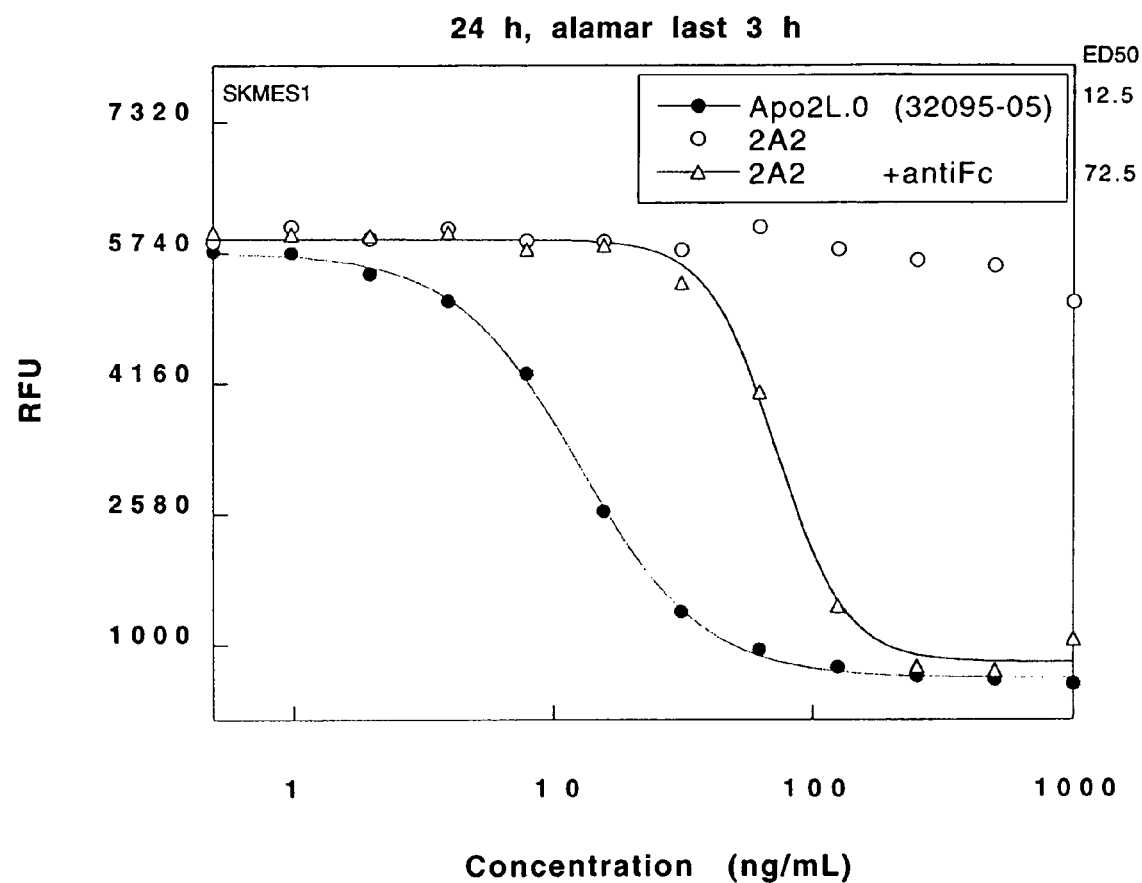
FIGS. 9A-9C are graphs showing the induction of cell death in SK-MES cells by varying concentrations of 2A2, 1G11, and 1E10 anti-DR4 antibodies.
Figure 9B:
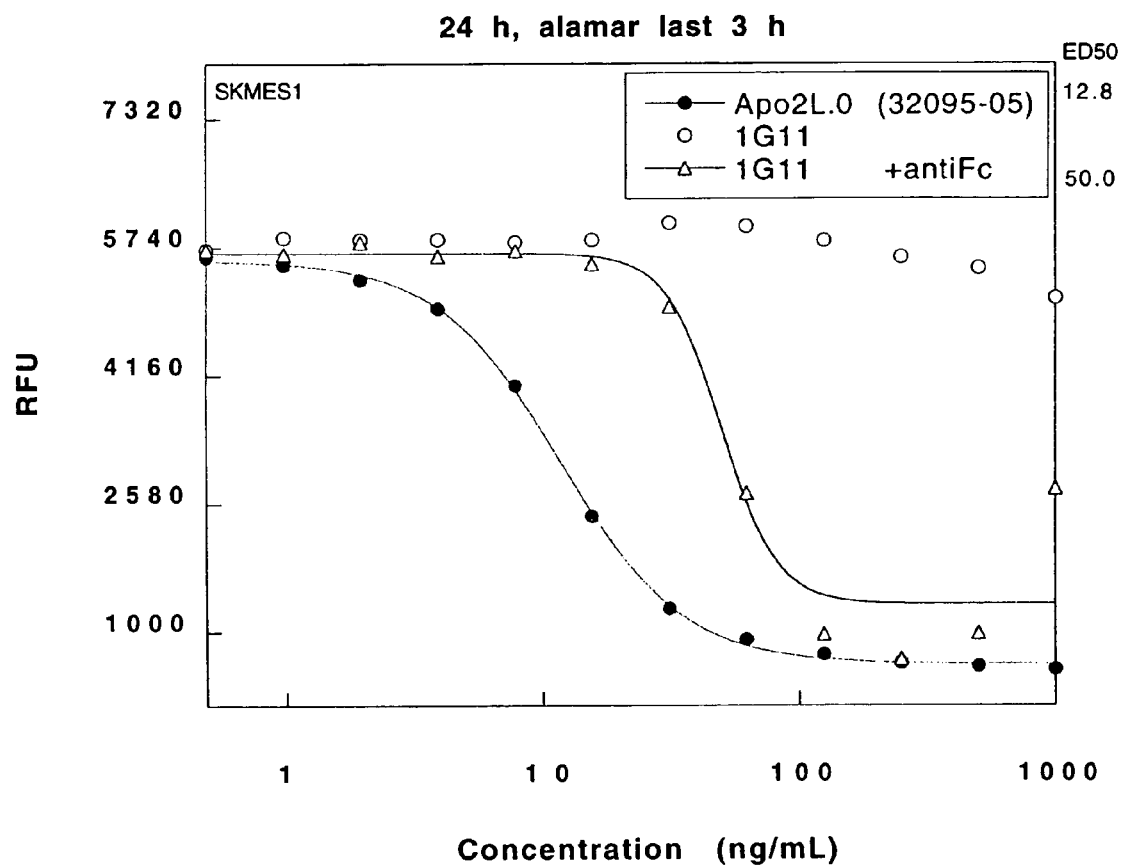
Figure 9C:
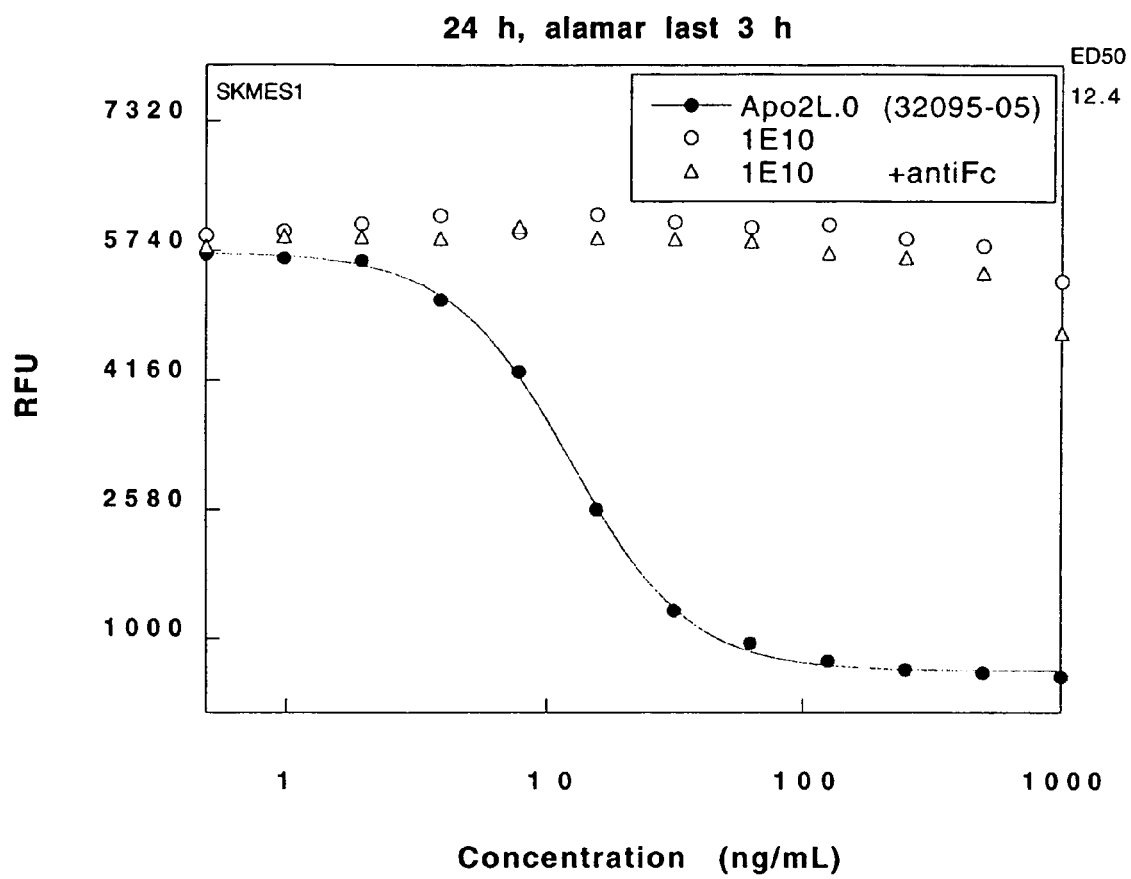
Figure 10A:
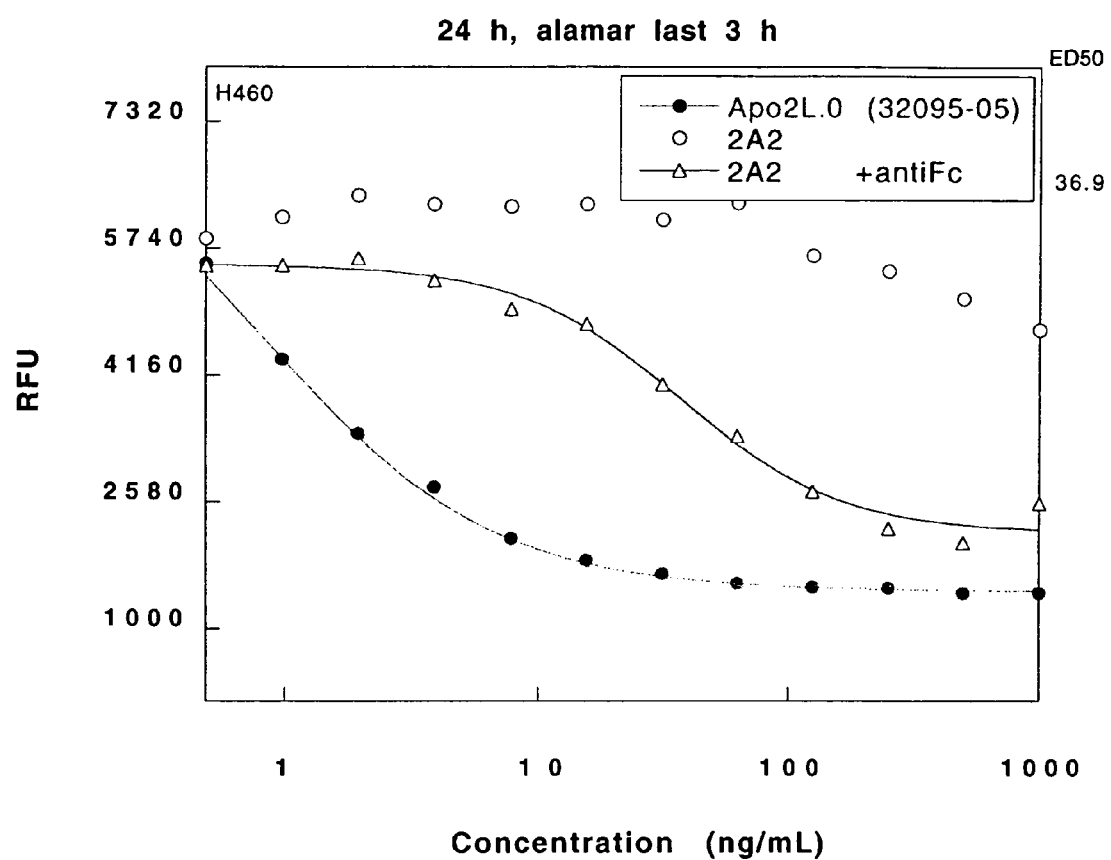
FIGS. 10A-10C are graphs showing the induction of cell death in H460 cells by varying concentrations of 2A2, 1G11, and 1E10 anti-DR4 antibodies.
Figure 10B:
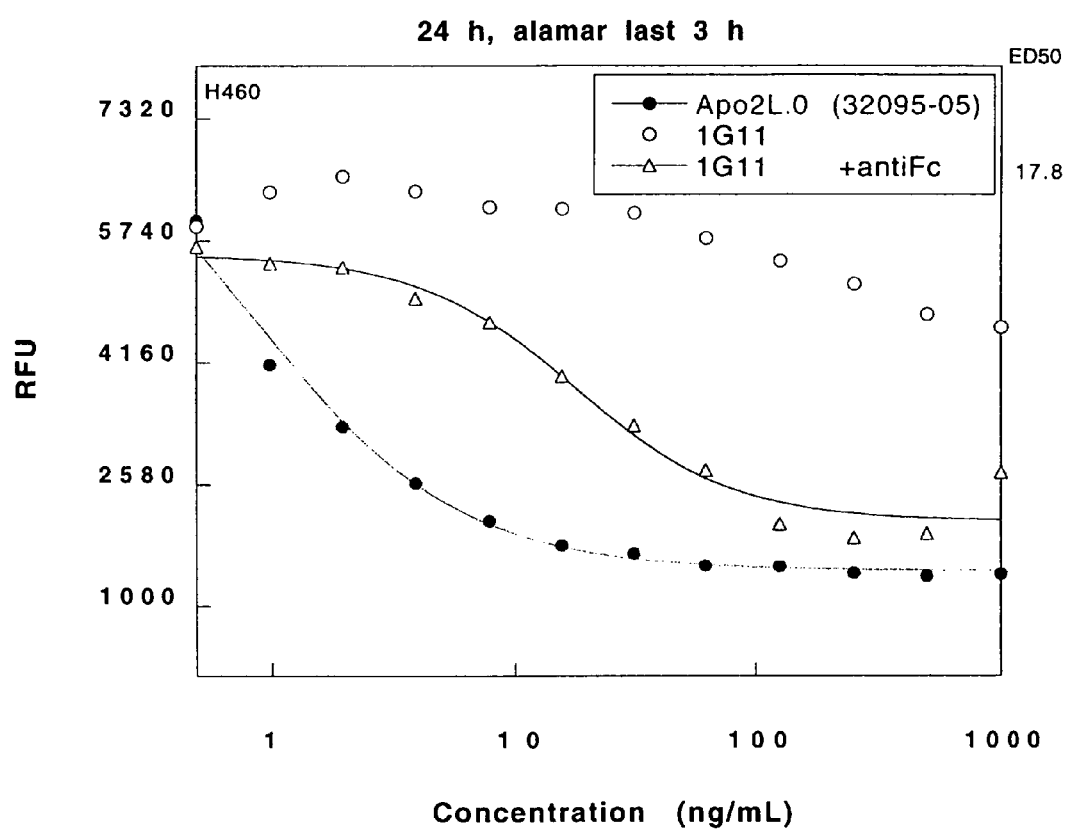
Figure 10C:
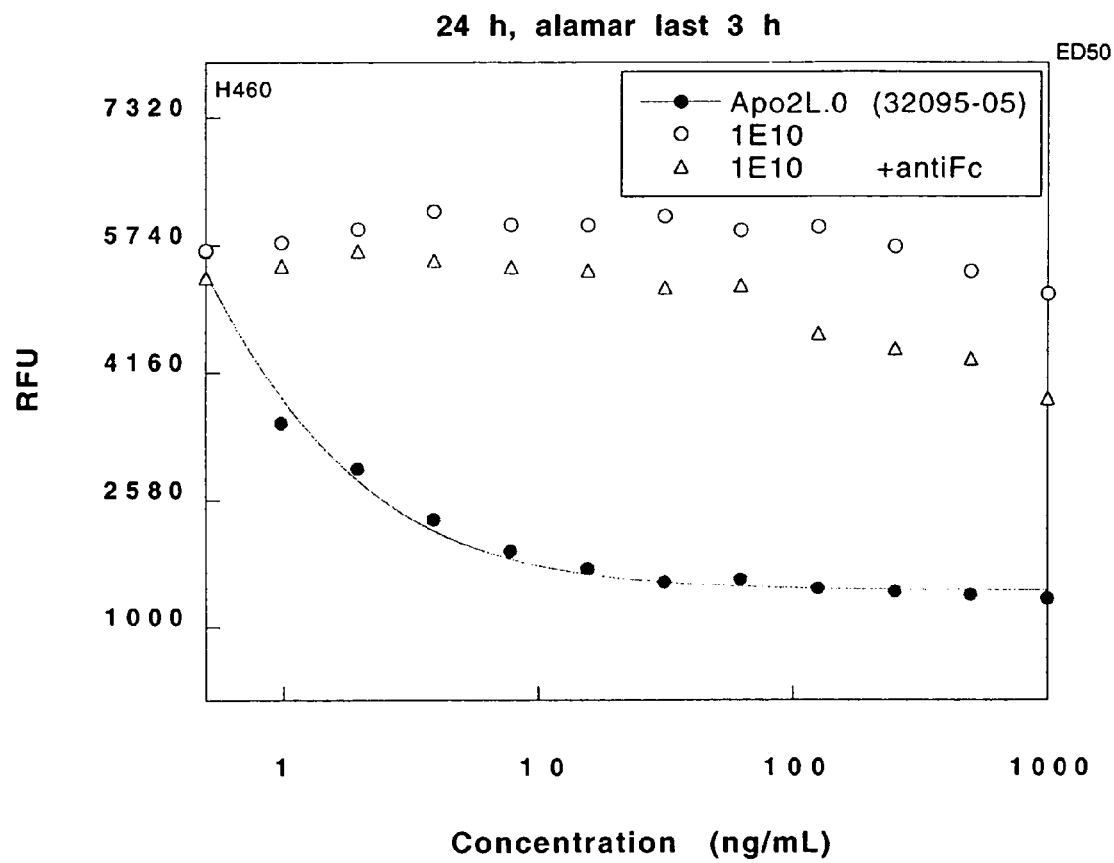
Figure 11A:
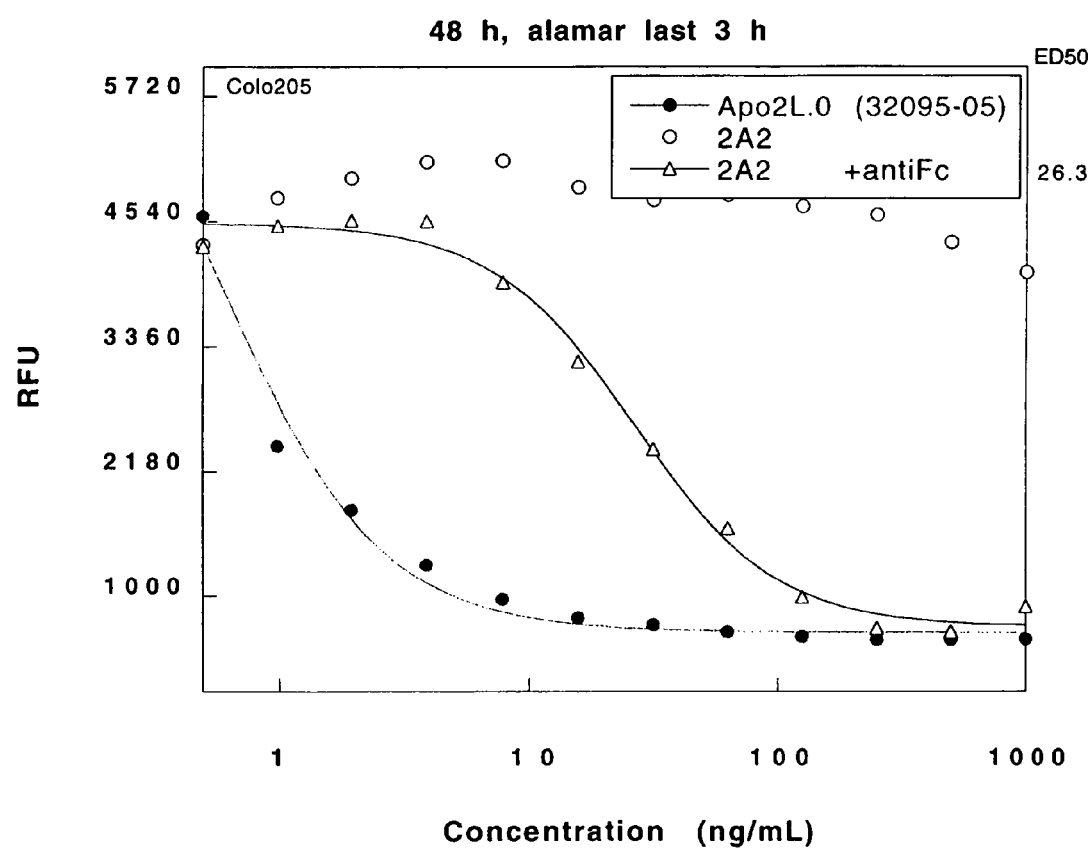
FIGS. 11A-11C are graphs showing the induction of cell death in Colo205 cells by varying concentrations of 2A2, 1G11, and 1E10 anti-DR4 antibodies.
Figure 11B:
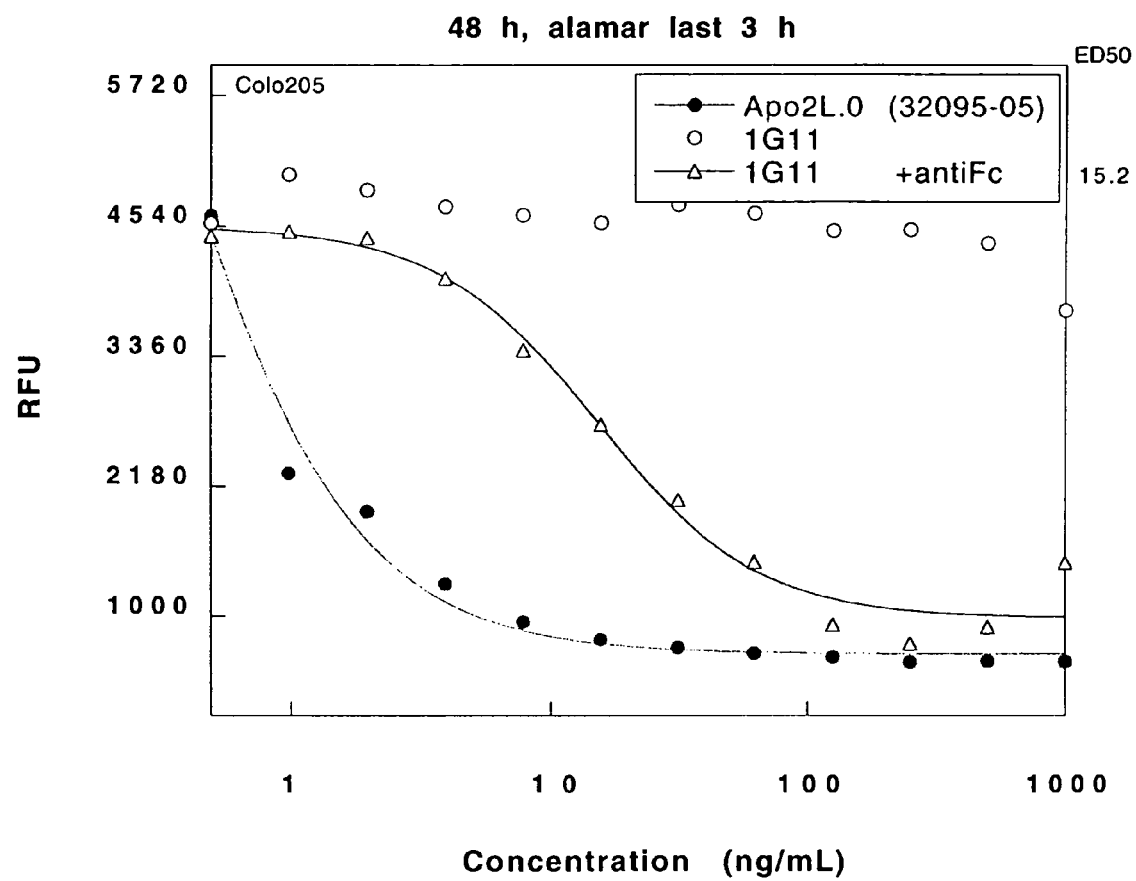
Figure 11C:
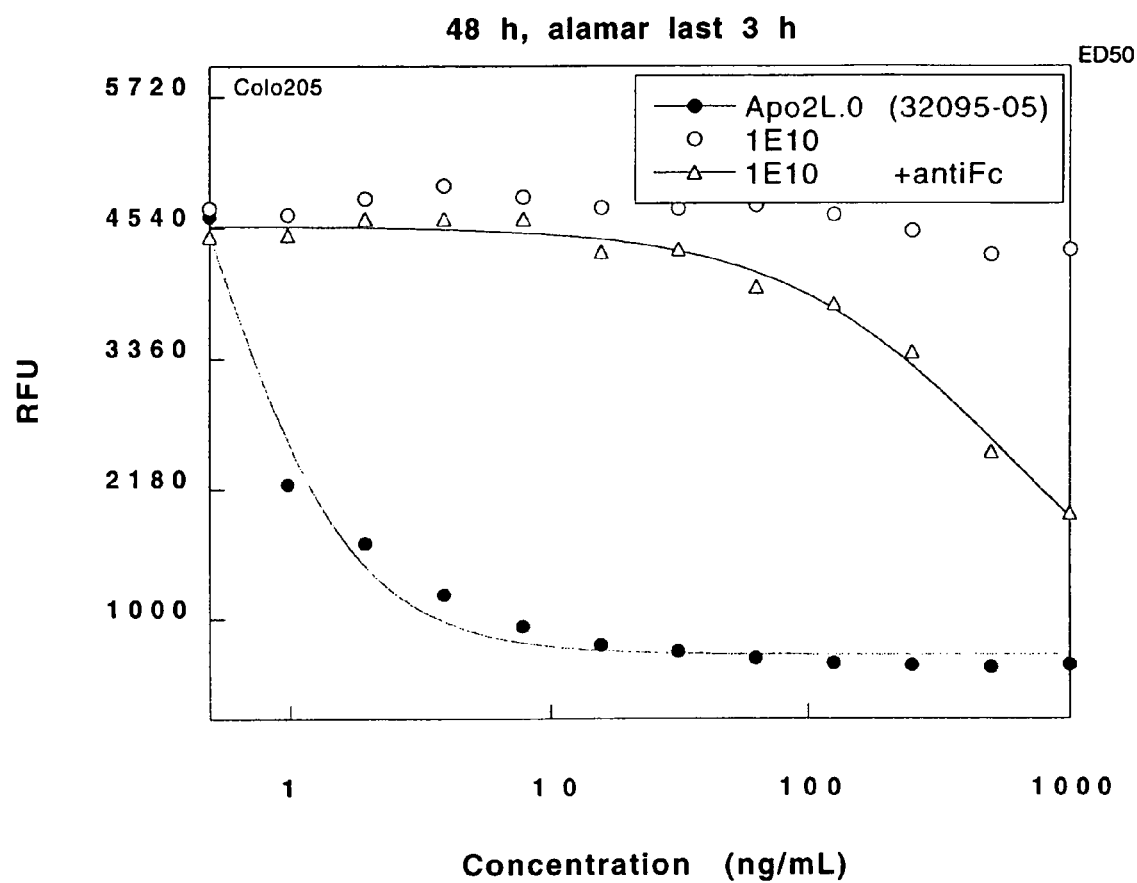
Figure 12A:
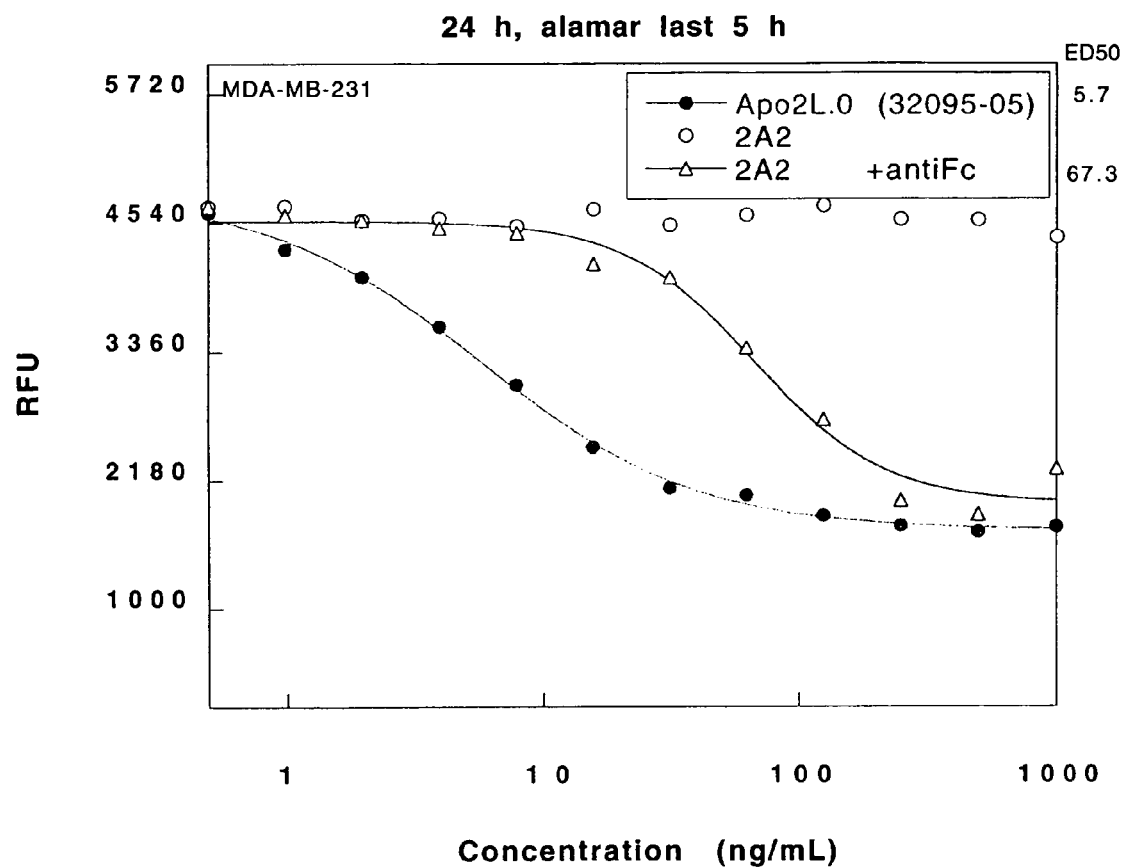
FIGS. 12A-12C are graphs showing the induction of cell death in MDA-MB-231 cells by varying concentrations of 2A2, 1G11, and 1E10 anti-DR4 antibodies.
Figure 12B:
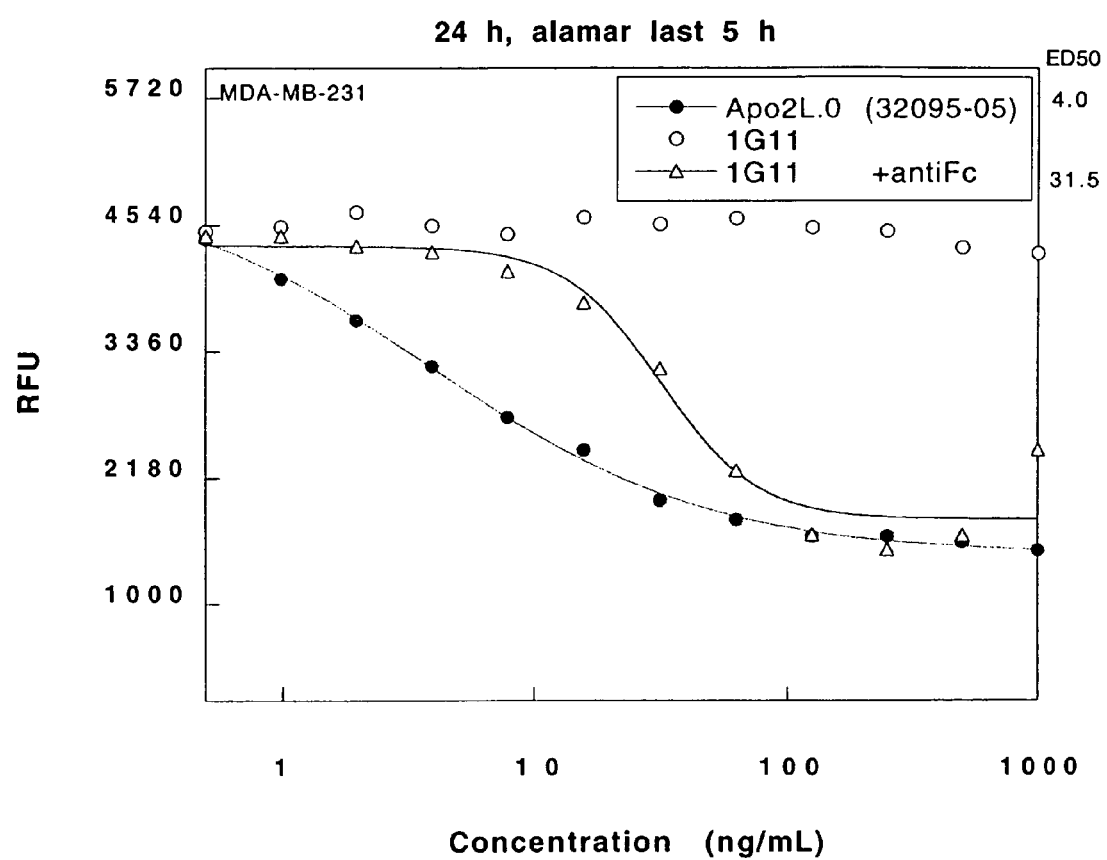
Figure 12C:
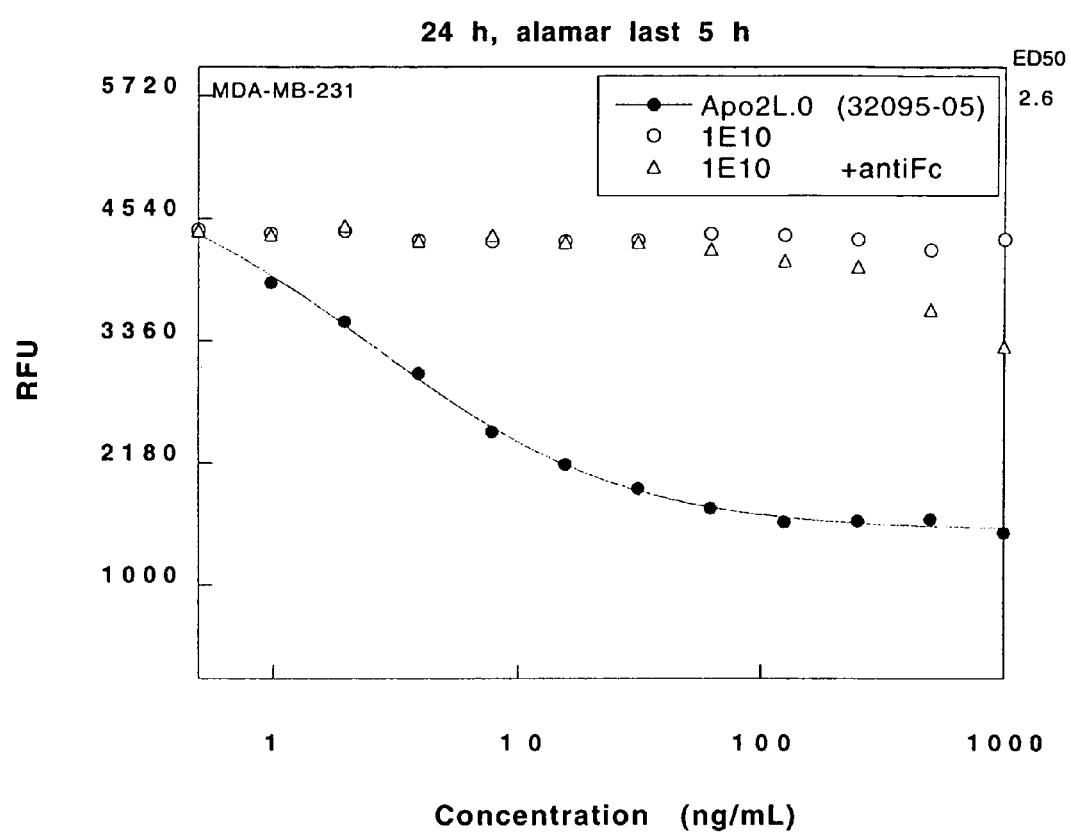
Figure 13A:
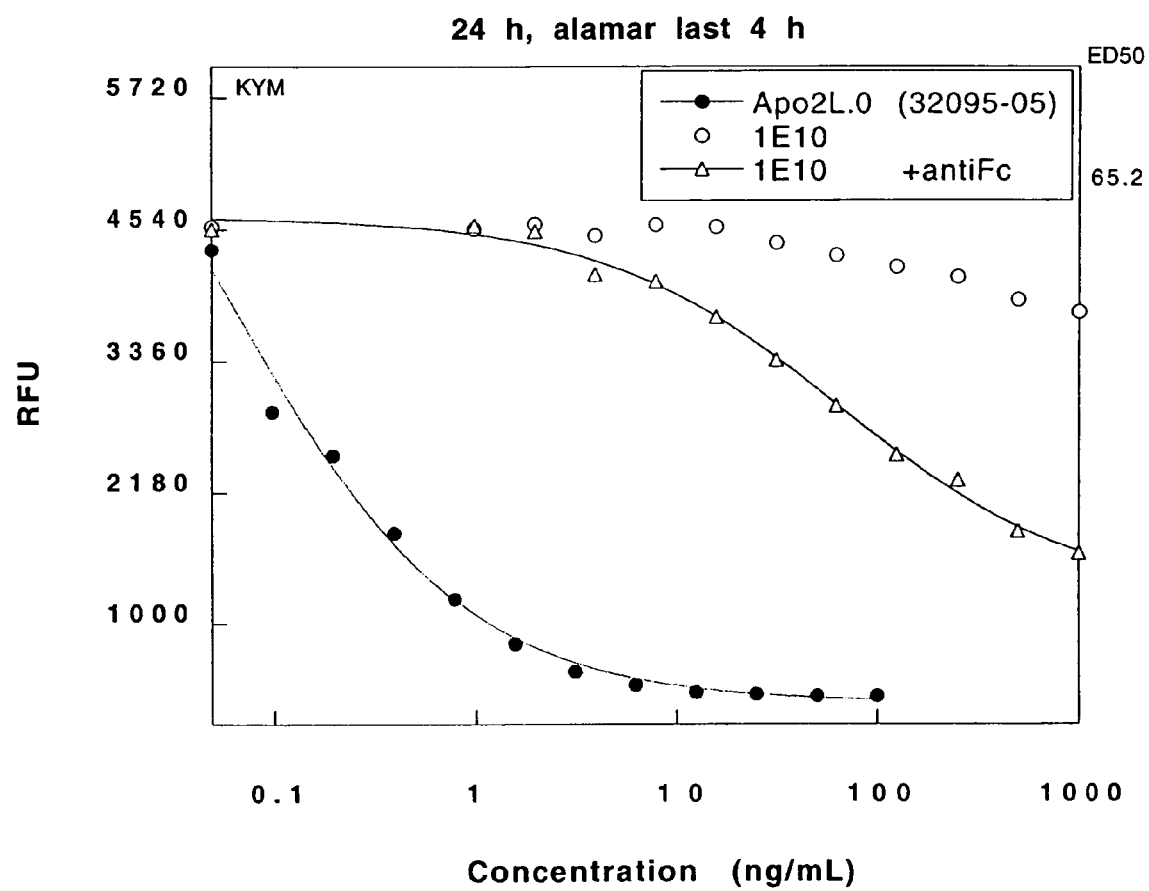
FIGS. 13A-13C are graphs showing the induction of cell death in KYM-1 rhabdomyosarcoma cells by varying concentrations of 2A2, 1G11, and 1E10 anti-DR4 antibodies.
Figure 13B:
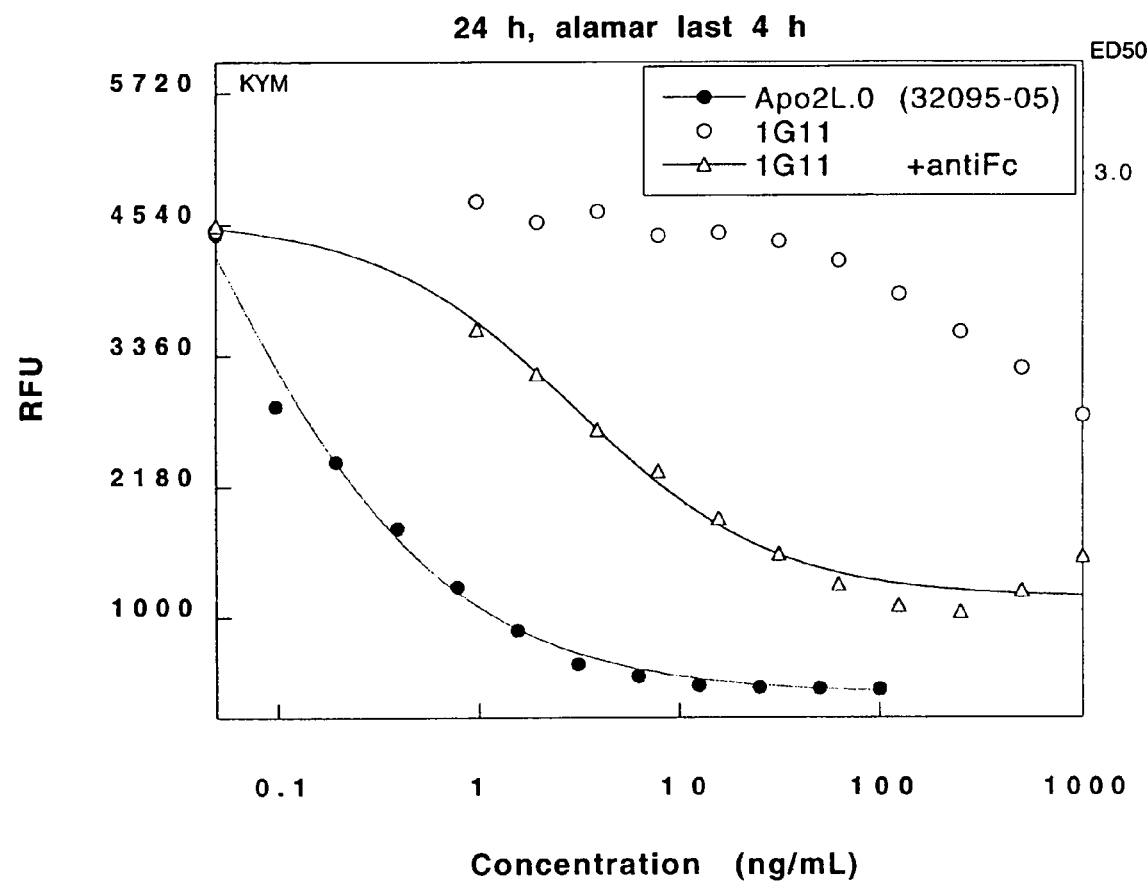
Figure 13C:
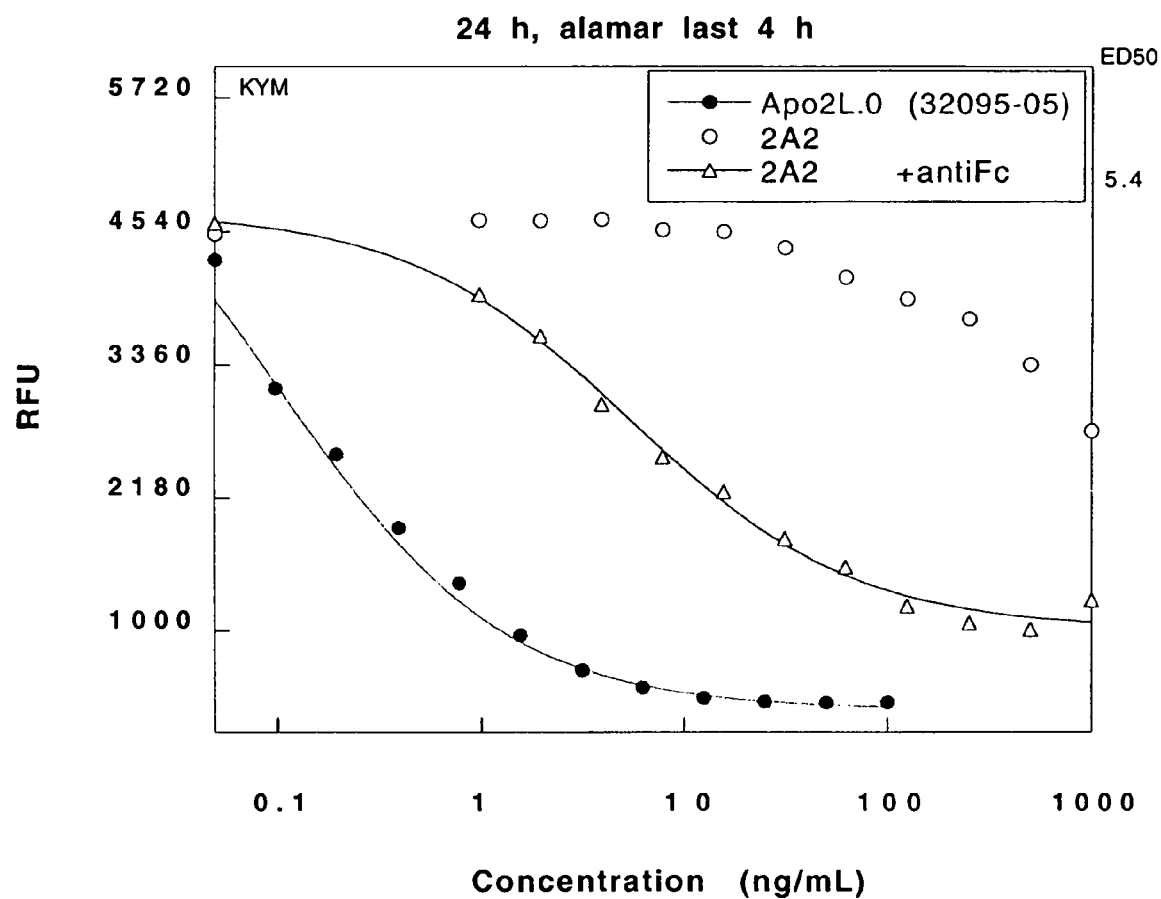

The results are shown in FIGS. 9A-9C; 10A-10C; 11A-11C; 12A-12C and 13A-13C. DR4 antibodies 2A2 and 1G11 demonstrated significant killing activity against all of the cell lines assayed, while DR4 antibody 1E10 showed significant killing activity against KYM-1 cells, some activity against H460, COLO205, and MDA-MB-231 cells, and little activity against SK– MES-1 cells. Activity of all three antibodies was observed particularly upon Fc crosslinking. All of the cell lines assayed express both DR4 and DR5 receptors, thus is not unexpected that the antibodies exhibited less cell killing than Apo2L since Apo2L recognizes and binds to both DR4 and DR5 receptors and the antibodies 2A2, 1G11, and 1E10 are selective for DR4.

Example 10

Caspase Activation by DR4 mAbs

Figure 14:
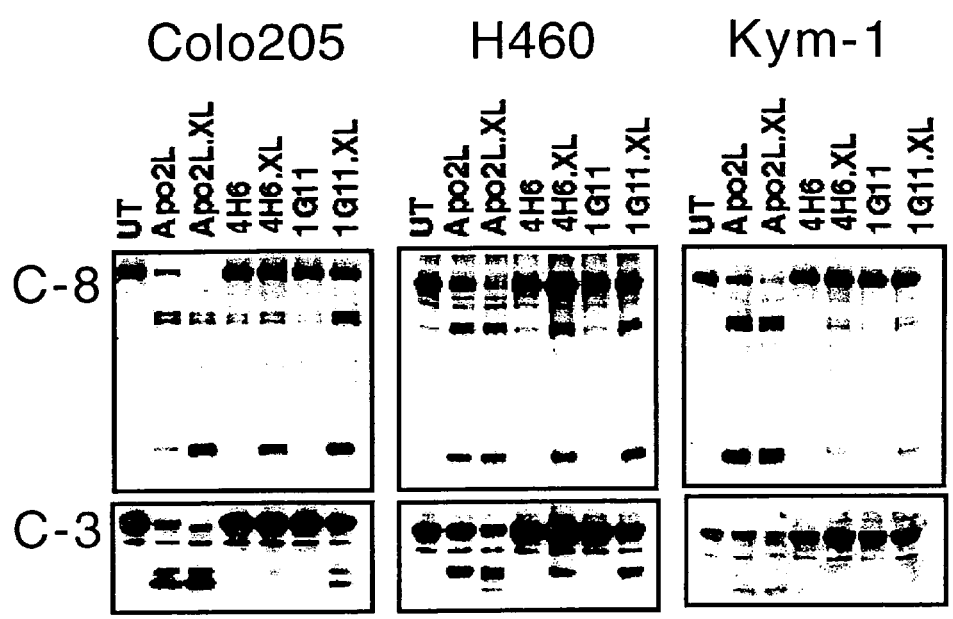
FIG. 14 shows the results of a caspase activation assay and western blot illustrating DR4 antibody activation of caspases 8 and 3.

The DR4 receptor is known to signal apoptosis activation through the apoptosis-initiator protease, caspase-8, and the apoptosis executioner protease caspase-3 (Kischkel et al., *Immunity*, 12:611 (2000)). To test activation of these caspases in cancer cells by DR4 monoclonal antibodies described herein, three cancer cell lines (COLO205 colon carcinoma, H460 non-small cell lung carcinoma, and Kym-1 rhabdomyosarcoma) were examined. The cells ($10^7$/lane) were incubated for 4 hours (1) without treatment (UT), (2) with Apo2L (1 µg/ml), (3) without Apo2L, (4) with cross-linked Apo2L ("Apo2L.XL") (cross-linked using M2 antibody, 1 µg/ml, Sigma, St. Louis, Mo., directed against an N-terminal Flag tag on the Apo-2 ligand polypeptide), or (5) with DR4 antibody 4H6 or 1G11 (1 µg/ml), (6) without DR4 antibody, or (7) with cross-linked DR4 antibody (indicated by "4H6.XL" or "1G11.XL", corss-linked using anti-Fc antibody (1 µg/ml). After one wash with phosphate buffered saline, the cells were lysed for 30 minutes on ice with lysis buffer (1% Triton X-100, 150 mM NaCl, 10% glycerol, 20 mM Tris-HCl, pH 7.5, 2 mM EDTA, 0.57 mM PMSF, protease inhibitor cocktail (complete™, Roche Molecular Biochemicals) and centrifuged at 15000×g for 15 minutes at 4° C. After several washes with the lysis buffer, the lysates were analyzed on 10% SDS-PAGE gels followed by electroblotting and detection through western blot with anti-caspase-8 or anti-caspase-3 antibodies (Uspstate Biotechnology, NY). The results are shown in FIG. 14.

Deposit of Material

The following materials have been deposited with the American Type Culture Collection, 10801 University Boulevard, Manassas, Va., USA (ATCC):

| Material | ATCC Dep. No. | Deposit Date |
|---|---|---|
| 4H6.17.8 | HB-12455 | Jan. 13, 1998 |
| 1E10.14.7 | PTA-3359 | May 8, 2001 |
| 2A2.16.7 | PTA-3360 | May 8, 2001 |
| 1G11.14.7 | PTA-3361 | May 8, 2001 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated, monoclonal human anti-DR4 receptor antibody that inhibits binding of Apo-2 ligand to the DR4 receptor, induces apoptosis upon binding to the DR4 receptor and binds to the same DR4 receptor epitope to which the monoclonal antibody produced by the hybridoma deposited as ATCC PTA-3359 binds, wherein said antibody binds to the DR4 receptor with a binding affinity of at least $10^{-8}$ $M^{-1}$ to $10^{-12}$ $M^{-1}$.

2. The anti-DR4 receptor antibody of claim 1 which is linked to one or more non-proteinaceous polymers selected from the group consisting of polyethylene glycol, polypropylene glycol, and polyoxyalkylene.

3. The anti-DR4 receptor antibody of claim 1 which is linked to a cytotoxic agent or enzyme.

4. The anti-DR4 receptor antibody of claim 1 which is linked to a radioisotope, fluorescent compound or chemiluminescent compound.

5. The anti-DR4 receptor antibody of claim 1 which is glycosylated.

6. The anti-DR4 receptor antibody of claim 1 which is unglycosylated.

7. The hybridoma deposited as ATCC PTA-3359.

8. The monoclonal antibody produced by the hybridoma deposited as ATCC PTA-3359.

9. A pharmaceutical composition comprising a therapeutically effective amount of the isolated monoclonal human anti-DR4 receptor antibody of claim 1 in admixture with a pharmaceutically acceptable carrier.

10. An isolated monoclonal human anti-DR4 receptor antibody that inhibits binding of Apo-2 ligand to the DR4 receptor, induces apoptosis upon binding to DR4 receptor, and binds to the same DR4 receptor epitope to which the monoclonal antibody produced by the hybridoma deposited as ATCC PTA-3360 binds, wherein said antibody binds to the DR4 receptor with a binding affinity of at least $10^{-8}$ $M^{-1}$ to $10^{-12}$ $M^{-1}$.

11. The anti-DR4 receptor antibody of claim 10 which is linked to one or more non-proteinaceous polymers selected from the group consisting of polyethylene glycol, polypropylene glycol, and polyoxyalkylene.

12. The anti-DR4 receptor antibody of claim 10 which is linked to a cytotoxic agent or enzyme.

13. The anti-DR4 receptor antibody of claim 10 which is linked to a radioisotope, fluorescent compound or chemiluminescent compound.

14. The anti-DR4 receptor antibody of claim 10 which is glycosylated.

15. The anti-DR4 receptor antibody of claim 10 which is unglycosylated.

16. The hybridoma deposited as ATCC PTA-3360.

17. The monoclonal antibody produced by the hybridoma deposited as ATCC PTA-3360.

18. A pharmaceutical composition comprising therapeutically effective amount of the isolated monoclonal human anti-DR4 receptor antibody of claim 10 in admixture with a pharmaceutically acceptable carrier.

19. An isolated monoclonal human anti-DR4 receptor antibody that inhibits binding of Apo-2 ligand to the DR4 receptor, induces apoptosis upon binding to the DR4 receptor and binds to the same DR4 receptor epitope to which the monoclonal antibody produced by the hybridoma deposited as ATCC PTA-3361 binds, wherein said antibody binds to the DR4 receptor with a binding affinity of at least $10^{-8}$ $M^{-1}$ to $10^{-12}$ $M^{-1}$.

20. The anti-DR4 receptor antibody of claim 19 which is linked to one or more non-proteinaceous polymers selected from the group consisting of polyethylene glycol, polypropylene glycol, and polyoxyalkylene.

21. The anti-DR4 receptor antibody of claim 19 which is linked to a cytotoxic agent or enzyme.

22. The anti-DR4 receptor antibody of claim 19 which is linked to a radioisotope, fluorescent compound or chemiluminescent compound.

23. The anti-DR4 receptor antibody of claim 19 which is glycosylated.

24. The anti-DR4 receptor antibody of claim 19 which is unglycosylated.

25. The hybridoma deposited as ATCC PTA-3361.

26. The monoclonal antibody produced by the hybridoma deposited as ATCC PTA-3361.

27. A pharmaceutical composition comprising therapeutically effective amount of the isolated monoclonal human anti-DR4 receptor antibody of claim 19 in admixture with a pharmaceutically acceptable carrier.

* * * * *

UNITED STATES PATENT AND TRADEMARK OFFICE
CERTIFICATE OF CORRECTION

PATENT NO. : 7,252,994 B2
APPLICATION NO. : 10/480730
DATED : August 7, 2007
INVENTOR(S) : Anan Chuntharapai et al.

It is certified that error appears in the above-identified patent and that said Letters Patent is hereby corrected as shown below:

In Claim 1, Column 65, lines 44-45, change "$10\char`^-8$ $M\char`^-1$ to $10\char`^-12$ $M\char`^-1$"
to -- $10\char`^8$ $M\char`^-1$ to $10\char`^12$ $M\char`^-1$ --.

In Claim 10, Column 66, lines 41-42, change "$10\char`^-8$ $M\char`^-1$ to $10\char`^-12$ $M\char`^-1$"
to -- $10\char`^8$ $M\char`^-1$ to $10\char`^12$ $M\char`^-1$ --.

In Claim 19, Column 67, lines 4-5, change "$10\char`^-8$ $M\char`^-1$ to $10\char`^-12$ $M\char`^-1$"
to -- $10\char`^8$ $M\char`^-1$ to $10\char`^12$ $M\char`^-1$ --.

Signed and Sealed this
Twenty-fourth Day of May, 2011

David J. Kappos
*Director of the United States Patent and Trademark Office*

SEQUENCE LISTING

```
<160> NUMBER OF SEQ ID NOS: 3

<210> SEQ ID NO 1
<211> LENGTH: 468
<212> TYPE: PRT
<213> ORGANISM: Homo sapiens

<400> SEQUENCE: 1

Met Ala Pro Pro Pro Ala Arg Val His Leu Gly Ala Phe Leu Ala
  1               5                  10                  15

Val Thr Pro Asn Pro Gly Ser Ala Ala Ser Gly Thr Glu Ala Ala
                 20                  25                  30

Ala Ala Thr Pro Ser Lys Val Trp Gly Ser Ser Ala Gly Arg Ile
                 35                  40                  45

Glu Pro Arg Gly Gly Gly Arg Gly Ala Leu Pro Thr Ser Met Gly
                 50                  55                  60

Gln His Gly Pro Ser Ala Arg Ala Arg Ala Gly Arg Ala Pro Gly
                 65                  70                  75

Pro Arg Pro Ala Arg Glu Ala Ser Pro Arg Leu Arg Val His Lys
                 80                  85                  90

Thr Phe Lys Phe Val Val Val Gly Val Leu Leu Gln Val Val Pro
                 95                 100                 105

Ser Ser Ala Ala Thr Ile Lys Leu His Asp Gln Ser Ile Gly Thr
                110                 115                 120

Gln Gln Trp Glu His Ser Pro Leu Gly Glu Leu Cys Pro Pro Gly
                125                 130                 135

Ser His Arg Ser Glu Arg Pro Gly Ala Cys Asn Arg Cys Thr Glu
                140                 145                 150
```

```
Gly Val Gly Tyr Thr Asn Ala Ser Asn Asn Leu Phe Ala Cys Leu
            155                 160                 165

Pro Cys Thr Ala Cys Lys Ser Asp Glu Glu Arg Ser Pro Cys
            170                 175                 180

Thr Thr Thr Arg Asn Thr Ala Cys Gln Cys Lys Pro Gly Thr Phe
            185                 190                 195

Arg Asn Asp Asn Ser Ala Glu Met Cys Arg Lys Cys Ser Thr Gly
            200                 205                 210

Cys Pro Arg Gly Met Val Lys Val Lys Asp Cys Thr Pro Trp Ser
            215                 220                 225

Asp Ile Glu Cys Val His Lys Glu Ser Gly Asn Gly His Asn Ile
            230                 235                 240

Trp Val Ile Leu Val Val Thr Leu Val Val Pro Leu Leu Leu Val
            245                 250                 255

Ala Val Leu Ile Val Cys Cys Cys Ile Gly Ser Gly Cys Gly Gly
            260                 265                 270

Asp Pro Lys Cys Met Asp Arg Val Cys Phe Trp Arg Leu Gly Leu
            275                 280                 285

Leu Arg Gly Pro Gly Ala Glu Asp Asn Ala His Asn Glu Ile Leu
            290                 295                 300

Ser Asn Ala Asp Ser Leu Ser Thr Phe Val Ser Glu Gln Gln Met
            305                 310                 315

Glu Ser Gln Glu Pro Ala Asp Leu Thr Gly Val Thr Val Gln Ser
            320                 325                 330

Pro Gly Glu Ala Gln Cys Leu Leu Gly Pro Ala Glu Ala Glu Gly
            335                 340                 345

Ser Gln Arg Arg Arg Leu Leu Val Pro Ala Asn Gly Ala Asp Pro
            350                 355                 360

Thr Glu Thr Leu Met Leu Phe Phe Asp Lys Phe Ala Asn Ile Val
            365                 370                 375

Pro Phe Asp Ser Trp Asp Gln Leu Met Arg Gln Leu Asp Leu Thr
            380                 385                 390

Lys Asn Glu Ile Asp Val Val Arg Ala Gly Thr Ala Gly Pro Gly
            395                 400                 405

Asp Ala Leu Tyr Ala Met Leu Met Lys Trp Val Asn Lys Thr Gly
            410                 415                 420

Arg Asn Ala Ser Ile His Thr Leu Leu Asp Ala Leu Glu Arg Met
            425                 430                 435

Glu Glu Arg His Ala Lys Glu Lys Ile Gln Asp Leu Leu Val Asp
            440                 445                 450

Ser Gly Lys Phe Ile Tyr Leu Glu Asp Gly Thr Gly Ser Ala Val
            455                 460                 465

Ser Leu Glu

<210> SEQ ID NO 2
<211> LENGTH: 1407
<212> TYPE: DNA
<213> ORGANISM: Homo sapiens

<400> SEQUENCE: 2
atggcgccac caccagctag agtacatcta ggtgcgttcc tggcagtgac        50
tccgaatccc gggagcgcag cgagtgggac agaggcagcc gcggccacac       100
ccagcaaagt gtgggctctc tccgcgggga ggattgaacc acgaggcggg       150
```

-continued

| | |
|---|---|
| ggccgaggag cgctccctac ctccatggga cagcacggac ccagtgcccg | 200 |
| ggcccgggca gggcgcgccc caggaccag gccggcgcgg gaagccagcc | 250 |
| ctcggctccg ggtccacaag accttcaagt ttgtcgtcgt cggggtcctg | 300 |
| ctgcaggtcg tacctagctc agctgcaacc atgatcaatc aattggcaca | 350 |
| aattggcaca cagcaatggg aacatagccc tttgggagag ttgtgtccac | 400 |
| caggatctca tagatcagaa cgtcctggag cctgtaaccg gtgcacagag | 450 |
| ggtgtgggtt acaccaatgc ttccaacaat ttgtttgctt gcctcccatg | 500 |
| tacagcttgt aaatcagatg aagaagagag aagtccctgc accacgacca | 550 |
| ggaacacagc atgtcagtgc aaaccaggaa cttccggaa tgacaattct | 600 |
| gctgagatgt gccggaagtg cagcacaggg tgccccagag gatggtcaa | 650 |
| ggtcaaggat tgtacgccct ggagtgacat cgagtgtgtc cacaaagaat | 700 |
| caggcaatgg acataatata tgggtgattt tggttgtgac tttggttgtt | 750 |
| ccgttgctgt tggtggctgt gctgattgtc tgttgttgca tcggctcagg | 800 |
| ttgtggaggg gaccccaagt gcatggacag ggtgtgtttc tggcgcttgg | 850 |
| gtctcctacg agggcctggg gctgaggaca atgctcacaa cgagattctg | 900 |
| agcaacgcag actcgctgtc cactttcgtc tctgagcagc aaatggaaag | 950 |
| ccaggagccg gcagatttga caggtgtcac tgtacagtcc caggggagg | 1000 |
| cacagtgtct gctgggaccg gcagaagctg aagggtctca gaggaggagg | 1050 |
| ctgctggttc cagcaaatgg tgctgacccc actgagactc tgatgctgtt | 1100 |
| ctttgacaag tttgcaaaca tcgtgcccctt tgactcctgg gaccagctca | 1150 |
| tgaggcagct ggacctcacg aaaaatgaga tcgatgtggt cagagctggt | 1200 |
| acagcaggcc caggggatgc cttgtatgca atgctgatga atgggtcaa | 1250 |
| caaaactgga cggaacgcct cgatccacac cctgctggat gccttggaga | 1300 |
| ggatggaaga gagacatgca aaagagaaga ttcaggacct cttggtggac | 1350 |
| tctggaaagt tcatctactt agaagatggc acaggctctg ccgtgtcctt | 1400 |
| ggagtga | 1407 |

<210> SEQ ID NO 3
<211> LENGTH: 281
<212> TYPE: PRT
<213> ORGANISM: Homo sapiens

<400> SEQUENCE: 3

Met Ala Met Met Glu Val Gln Gly Gly Pro Ser Leu Gly Gln Thr
1               5                   10                  15

Cys Val Leu Ile Val Ile Phe Thr Val Leu Leu Gln Ser Leu Cys
                20                  25                  30

Val Ala Val Thr Tyr Val Tyr Phe Thr Asn Glu Leu Lys Gln Met
                35                  40                  45

Gln Asp Lys Tyr Ser Lys Ser Gly Ile Ala Cys Phe Leu Lys Glu
                50                  55                  60

Asp Asp Ser Tyr Trp Asp Pro Asn Asp Glu Glu Ser Met Asn Ser
                65                  70                  75

Pro Cys Trp Gln Val Lys Trp Gln Leu Arg Gln Leu Val Arg Lys
                80                  85                  90

Met Ile Leu Arg Thr Ser Glu Glu Thr Ile Ser Thr Val Gln Glu

-continued

```
                        95                  100                 105
Lys Gln Gln Asn Ile Ser Pro Leu Val Arg Glu Arg Gly Pro Gln
                110                 115                 120

Arg Val Ala Ala His Ile Thr Gly Thr Arg Gly Arg Ser Asn Thr
                125                 130                 135

Leu Ser Ser Pro Asn Ser Lys Asn Glu Lys Ala Leu Gly Arg Lys
                140                 145                 150

Ile Asn Ser Trp Glu Ser Ser Arg Ser Gly His Ser Phe Leu Ser
                155                 160                 165

Asn Leu His Leu Arg Asn Gly Glu Leu Val Ile His Glu Lys Gly
                170                 175                 180

Phe Tyr Tyr Ile Tyr Ser Gln Thr Tyr Phe Arg Phe Gln Glu Glu
                185                 190                 195

Ile Lys Glu Asn Thr Lys Asn Asp Lys Gln Met Val Gln Tyr Ile
                200                 205                 210

Tyr Lys Tyr Thr Ser Tyr Pro Asp Pro Ile Leu Leu Met Lys Ser
                215                 220                 225

Ala Arg Asn Ser Cys Trp Ser Lys Asp Ala Glu Tyr Gly Leu Tyr
                230                 235                 240

Ser Ile Tyr Gln Gly Gly Ile Phe Glu Leu Lys Glu Asn Asp Arg
                245                 250                 255

Ile Phe Val Ser Val Thr Asn Glu His Leu Ile Asp Met Asp His
                260                 265                 270

Glu Ala Ser Phe Phe Gly Ala Phe Leu Val Gly
                275                 280
```